(12) United States Patent
Zhou et al.

(10) Patent No.: US 10,510,143 B1
(45) Date of Patent: Dec. 17, 2019

(54) SYSTEMS AND METHODS FOR GENERATING A MASK FOR AUTOMATED ASSESSMENT OF EMBRYO QUALITY

(71) Applicant: Progyny, Inc., New York, NY (US)

(72) Inventors: Yan Zhou, Santa Clara, CA (US); Martin T. Chian, Los Altos, CA (US); Lei Tan, El Cerrito, CA (US); Daniel E. Koppel, San Jose, CA (US)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 15/271,054

(22) Filed: Sep. 20, 2016

Related U.S. Application Data

(60) Provisional application No. 62/221,537, filed on Sep. 21, 2015.

(51) Int. Cl.
*G06T 7/00* (2017.01)
*G06T 7/60* (2017.01)
*G01N 33/483* (2006.01)

(52) U.S. Cl.
CPC ....... *G06T 7/0012* (2013.01); *G01N 33/4833* (2013.01); *G06T 7/60* (2013.01); *G06T 2207/10056* (2013.01); *G06T 2207/30044* (2013.01)

(58) Field of Classification Search
CPC ...... C12M 21/06; C12M 41/46; C12M 41/48; C12M 41/36; C12M 41/14; G06K 9/00147; G06K 9/00127; G06K 9/0014; G06K 9/00557; G01N 33/5005; G01N 15/1475; G02B 21/365; G02B 21/0004; G06T 2207/10056; G06T 2207/30044; G06T 2207/30004
See application file for complete search history.

(56) References Cited

U.S. PATENT DOCUMENTS 7,963,906 B2 * 6/2011 Wong .................. C12N 5/0604
435/375
8,323,177 B2 * 12/2012 Wong .................. C12N 5/0604
435/375

(Continued)

FOREIGN PATENT DOCUMENTS

WO WO/2007/144001 12/1907

OTHER PUBLICATIONS

El-Toukhy, T. et al. (2009) "A multi-centre randomised controlled study of pre-IVF outpatient hysteroscopy in women with recurrent IVF implantation failure: Trial of Outpatient Hysteroscopy—[TROPHY] in IVF," *Reproductive Health* 6, 20-20.

(Continued)

*Primary Examiner* — Michael S Osinski
(74) *Attorney, Agent, or Firm* — Medlen & Carroll, LLP

(57) ABSTRACT

Systems and methods for generating a mask for automated assessment of embryo quality are disclosed herein. The method for generating a mask for automated assessment of embryo quality can include receiving an image, including a plurality of pixels, of a human embryo from an imaging system. A pixel can be selected and features of the selected pixel can be determined by generating a plurality of random boxes of random sizes and at random locations about the selected pixel. The selected pixel can be identified as one of: inside of a mask area; and outside of the mask area based on the determined features.

9 Claims, 28 Drawing Sheets

(56) References Cited

U.S. PATENT DOCUMENTS

| | | | | |
|---|---|---|---|---|
| 8,337,387 | B2* | 12/2012 | Wong | C12N 5/0604 600/33 |
| 8,515,143 | B2* | 8/2013 | Oonishi | G06K 9/00147 382/128 |
| 8,721,521 | B2* | 5/2014 | Wong | C12N 5/0604 600/33 |
| 8,744,775 | B2* | 6/2014 | Timmis | G01J 3/02 702/19 |
| 8,951,184 | B2* | 2/2015 | Wong | C12Q 1/02 600/33 |
| 8,989,475 | B2* | 3/2015 | Wong | C12N 5/0604 382/128 |
| 9,228,931 | B2* | 1/2016 | Wong | C12N 5/0604 |
| 9,404,908 | B2* | 8/2016 | Chavez | A01N 1/0226 |
| 9,482,659 | B2* | 11/2016 | Loewke | G01N 35/00584 |
| 9,678,018 | B2* | 6/2017 | Takahashi | G01N 21/255 |
| 9,778,263 | B2* | 10/2017 | Bhaumik | G01N 33/57492 |
| 2005/0202404 | A1* | 9/2005 | Wittenberg | G06K 9/0014 435/4 |
| 2006/0160065 | A1* | 7/2006 | Timmis | A01C 1/00 435/4 |
| 2008/0247628 | A1* | 10/2008 | Ramsing | G06K 9/00127 382/133 |
| 2010/0041090 | A1* | 2/2010 | Ramsing | C12N 5/0604 435/29 |
| 2010/0195877 | A1* | 8/2010 | Oonishi | G06K 9/00147 382/128 |
| 2011/0092762 | A1* | 4/2011 | Wong | C12N 5/0604 600/34 |
| 2011/0105834 | A1* | 5/2011 | Wong | C12N 5/0604 600/34 |
| 2011/0165609 | A1* | 7/2011 | Ramsing | C12M 21/06 435/29 |
| 2012/0002034 | A1* | 1/2012 | Matsunobu | G02B 21/125 348/79 |
| 2012/0123193 | A1* | 5/2012 | Posillico | G01N 33/6806 600/34 |
| 2012/0263369 | A1* | 10/2012 | Xie | G06T 7/0012 382/134 |
| 2013/0023041 | A1* | 1/2013 | Greenberger | C12M 23/12 435/288.3 |
| 2013/0258090 | A1* | 10/2013 | Steinmeyer | G02B 21/361 348/79 |
| 2013/0337487 | A1* | 12/2013 | Loewke | G01N 33/4833 435/29 |
| 2014/0087415 | A1* | 3/2014 | Ramsing | G06K 9/0014 435/29 |
| 2014/0349334 | A1* | 11/2014 | Chavez | G01N 33/4833 435/34 |
| 2015/0262356 | A1* | 9/2015 | Yoshihara | G06T 7/0012 382/133 |
| 2015/0268227 | A1* | 9/2015 | Tan | G01N 15/1463 435/29 |
| 2016/0290930 | A1* | 10/2016 | Takahashi | G01N 21/255 |
| 2016/0349232 | A1* | 12/2016 | Shults | G01N 33/4833 |
| 2017/0091948 | A1* | 3/2017 | Paradkar | G06T 7/0081 |
| 2017/0178321 | A1* | 6/2017 | Nieves Alicea | G06K 9/4604 |
| 2017/0215814 | A1* | 8/2017 | Cales | A61B 5/743 |
| 2017/0323431 | A1* | 11/2017 | Sarkar | G06T 5/003 |

OTHER PUBLICATIONS

Fenwick, J. et al. (2002) "Time from insemination to first cleavage predicts developmental competence of human preimplantation embryos in vitro," *Human Reproduction* 17(2), 407-412.

Fragouli, E. et al. (2010) "Comprehensive chromosome screening of polar bodies and blastocysts from couples experiencing repeated implantation failure," *Fertility and Sterility* 94(3), 875-887.

Lemmen, J. G. et al. (2008) "Kinetic markers of human embryo quality using time-lapse recordings of IVF/ICSI—fertilized oocytes," *Reproductive Biomedicine Online* 17(3), 385-391.

Lundin, K. et al. (2001) "Early embryo cleavage is a strong indicator of embryo quality in human IVF," *Human Reproduction* 16(12), 2652-2657.

Manipalviratn, S. et al. (2009) "Imprinting disorders and assisted reproductive technology," *Fertility and Sterility* 91(2), 305-315.

Mastenbroek, S. et al. (2007) "In Vitro Fertilization with Preimplantation Genetic Screening," *New England Journal of Medicine* 357(1), 9-17.

Milki, A. A. et al. (2000) "Comparison of blastocyst transfer with day 3 embryo transfer in similar patient populations," *Fertility and Sterility* 73(1), 126-129.

Milki, A. A. et al. (2002) "Accuracy of day 3 criteria for selecting the best embryos," *Fertility and Sterility* 77(6), 1191-1195.

Nagy, Z. P. et al. (1994) "Fertilization and early embryology: Time-course of oocyte activation, pronucleus formation and cleavage in human oocytes fertilized by intracytoplasmic sperm injection," *Human Reproduction* 9(9), 1743-1748.

Payne, D. et al. (1997) "Preliminary observations on polar body extrusion and pronuclear formation in human oocytes using time-lapse Video cinematographx," *Human Reproduction* 12(3), 532-541.

Rijnders, P. M. et al. (1998) "The predictive value of day 3 embryo morphology regarding blastocyst formation, pregnancy and implantation rate after day 5 transfer following in-vitro fertilization or intracytoplasmic sperm injection," Human Reproduction 13(1O), 2869-2873.

Taft, R. A. (2008) "Virtues and limitations of the preimplantation mouse embryo as a model system," *Theriogenology* 69(1), 10-16.

Vanneste, E. et al. (2009) "Chromosome instability is common in human cleavage-stage embryos," *Nature Medicine* 15, 577.

* cited by examiner

SYSTEMS AND METHODS FOR GENERATING A MASK FOR AUTOMATED ASSESSMENT OF EMBRYO QUALITY

CROSS-REFERENCES TO RELATED APPLICATIONS

This application claims the benefit of U.S. Provisional Application No. 62/221,537, filed on Sep. 21, 2015, and entitled "SYSTEMS AND METHODS FOR GENERATING A MASK FOR AUTOMATED ASSESSMENT FOR EMBRYO QUALITY", the entirety of which is hereby incorporated by reference herein.

BACKGROUND

Infertility is a common health problem that affects 10-15% of couples of reproductive-age. In the United States alone in the year 2006, approximately 140,000 cycles of in vitro fertilization (IVF) were performed (cdc.gov/art). This resulted in the culture of more than a million embryos annually with variable, and often ill-defined, potential for implantation and development to term. The live birth rate, per cycle, following IVF was just 29%, while on average 30% of live births resulted in multiple gestations (cdc.gov/art). Multiple gestations have well-documented adverse outcomes for both the mother and fetuses, such as miscarriage, pre-term birth, and low birth rate. Potential causes for failure of IVF are diverse; however, since the introduction of IVF in 1978, one of the major challenges has been to identify the embryos that are most suitable for transfer and most likely to result in term pregnancy.

Traditionally in IVF clinics, human embryo viability has been assessed by simple morphologic observations such as the presence of uniformly-sized, mononucleate blastomeres and the degree of cellular fragmentation (Rijinders P M, Jansen C A M. (1998) Hum Reprod 13:2869-73; Milki A A, et al. (2002) Fertil Steril 77:1191-5). More recently, additional methods such as extended culture of embryos (to the blastocyst stage at day 5) and analysis of chromosomal status via preimplantation genetic diagnosis (PGD) have also been used to assess embryo quality (Milki A, et al. (2000) Fertil Steril 73:126-9; Fragouli E, (2009) Fertil Steril June 21 [EPub ahead of print]; El-Toukhy T, et al. (2009) Hum Reprod 6:20; Vanneste E, et al. (2009) Nat Med 15:577-83). However, potential risks of these methods also exist in that they prolong the culture period and disrupt embryo integrity (Manipalviratn S, et al. (2009) Fertil Steril 91:305-15; Mastenbroek S, et al. (2007) N Engl J Med. 357:9-17).

Recently it has been shown that time-lapse imaging can be a useful tool to observe early embryo development. Some methods have used time-lapse imaging to monitor human embryo development following intracytoplasmic sperm injection (ICSI) (Nagy et al. (1994) Human Reproduction. 9(9):1743-1748; Payne et al. (1997) Human Reproduction. 12:532-541). Polar body extrusion and pro-nuclear formation were analyzed and correlated with good morphology on day 3. However, no parameters were correlated with blastocyst formation or pregnancy outcomes. Other methods have looked at the onset of first cleavage as an indicator to predict the viability of human embryos (Fenwick, et al. (2002) Human Reproduction, 17:407-412; Lundin, et al. (2001) Human Reproduction 16:2652-2657). However, these methods do not recognize the importance of the duration of cytokinesis or time intervals between early divisions.

Other methods have used time-lapse imaging to measure the timing and extent of cell divisions during early embryo development (WO 2007/144001). However, these methods disclose only a basic and general method for time-lapse imaging of bovine embryos, which are substantially different from human embryos in terms of developmental potential, morphological behavior, molecular and epigenetic programs, and timing and parameters surrounding transfer. For example, bovine embryos take substantially longer to implant compared to human embryos (30 days and 9 days, respectively). (Taft, (2008) Theriogenology 69(1):10-16. Moreover, no specific imaging parameters or time intervals are disclosed that might be predictive of human embryo viability.

More recently, time-lapse imaging has been used to observe human embryo development during the first 24 hours following fertilization (Lemmen et al. (2008) Reproductive BioMedicine Online 17(3):385-391). The synchrony of nuclei after the first division was found to correlate with pregnancy outcomes. However, this work concluded that early first cleavage was not an important predictive parameter, which contradicts previous studies (Fenwick, et al. (2002) Human Reproduction 17:407-412; Lundin, et al. (2001) Human Reproduction 16:2652-2657).

Finally, no studies have validated the imaging parameters through correlation with the molecular programs or chromosomal composition of the embryos. Methods of human embryo evaluation are thus lacking in several respects, including their inability to conduct the imaging and evaluation in an automated fashion.

It is against this background that a need arose to develop the apparatus, method, and system for the improved viability prediction of embryos, oocytes, and stem cells described herein.

BRIEF SUMMARY

One aspect of the present disclosure relates to a method for generating an embryo mask applied to a series of time-lapse images of human embryos generated with an imaging system. The method includes receiving an image of the human embryo from the imaging system, which image includes a plurality of pixels, selecting a pixel from the plurality of pixels, determining features of the selected pixel by generating a plurality of random boxes of random sizes and at random locations about the selected pixel, and identifying, based on the determined features, the selected pixel as one of: inside of a mask area; and outside of the mask area.

In some embodiments, the size of each of the random boxes is randomly generated within a predetermined range. In some embodiments, the predetermined range includes a first portion specifying a range of lengths of the random boxes and a second portion specifying a range of widths of the random boxes. In some embodiments, the predetermined range specifies limits for the size of the random boxes. In some embodiments, the predetermined range specifies boxes sized from [3, 1] pixels to [3, 7] pixels.

In some embodiments, the random locations of the random boxes are randomly generated within a predetermined range of acceptable locations about the pixel. In some embodiments, the predetermined range of acceptable locations is defined by a radius extending from the pixel. In some embodiments, a length of the radius is up to 7 pixels.

In some embodiments, determining features of the selected pixel by generating the plurality of random boxes includes: identifying an image attribute for each of the generated random boxes; and pairing each of the generated random boxes with another of the generated random boxes. In some embodiments, pairing each of the generated random boxes with another of the generated random boxes includes generating 50 pairs of boxes. In some embodiments, determining features of the selected pixel by generating the plurality of random boxes further includes comparing the image attribute of the paired random boxes with each other.

In some embodiments, identifying the selected pixel as one of: inside of the mask area; and outside of the mask area, includes applying results of the comparison of the image attribute of the paired random boxes to a statistical model. In some embodiments, the results of the comparison of the image attribute of the paired random boxes are applied to the statistical model with a classifier. In some embodiments, the classifier includes one of: a Random Forest classifier; an AdaBoost classifier; a Naïve Bayes classifier; Boosting Tree, and a Support Vector Machine.

In some embodiments the method includes: iteratively selecting pixels from the plurality of pixels; determining features of the iteratively selected pixels by generating another plurality of random boxes of random sizes and at random locations about each the iteratively selected pixels; and identifying, based on the determined features, each of the iteratively selected pixels as one of: inside of the mask area; and outside of the mask area. In some embodiments, the method further includes: generating a preliminary mask, which preliminary mask is generated based on a designation of pixels as one of inside of the mask area; and outside of the mask area, and which preliminary mask includes a plurality of components formed from the pixels; determining a first connected component from the plurality of components; designating the first connected component as the first mask; and eliminating the plurality components other than the first connected component from the first mask.

In some embodiments, the first connected component is the largest component of the plurality of components. In some embodiments the method includes generating a final mask. In some embodiments, generated the final mask includes: identifying at least one hole in the first mask; and filing the identified at least one hole in the first mask. In some embodiments, the method includes applying or superimposing the final mask to or over the received image. In some embodiments, applying the final mask over the received image enables identification of at least one of: cavitation; and hatching. In some embodiments the method includes identifying portions of a multi-well culture dish well containing the human embryo that are visible in the image of the human embryo; and removing the visible portions of a multi-well culture dish well from the image of the human embryo.

One aspect of the present disclosure relates to a method for determining viability of human embryos with an imaging system. The method includes: receiving an image of a well including the human embryo from the imaging system; generating an embryo mask for the received image, which embryo mask distinguishes between a first portion of the image and a second portion of the image, which first portion contains the image of the embryo, and which second portion does not contain the image of the embryo; detecting a feature of the image based on the embryo mask; and generating a viability prediction based on the detected image based feature.

In some embodiments, the image based feature relates to at least one of: embryo image area; cavity image area; a change in embryo image area over time; a change in cavity image area over time; embryo image perimeter; and convex hull. In some embodiments, the image based feature relates to at least one of: cavitation; hatching; embryo expansion; and embryo collapse. In some embodiments, the image-based features relate to at least one of: an area of the embryo; an area of a cavity of the embryo; a perimeter of the embryo; and a convex hull. In some embodiments, the viability prediction includes a prediction of euploidy in the human embryo. In some embodiments, the viability prediction includes a prediction of aneuploidy in the human embryo.

In some embodiments, generating the mask further includes: generating a plurality of random boxes; and identifying a portion of the image as one of: inside of a mask area; and outside of the mask area based on features from the random boxes. In some embodiments, the method includes: iteratively selecting pixels from the plurality of pixels; determining features of the iteratively selected pixels by generating another plurality of random boxes of random sizes and at random locations about each the iteratively selected pixels; and identifying, based on the determined features, each of the iteratively selected pixels as one of: inside of a mask area; and outside of the mask area.

One aspect of the present disclosure relates to a method for determining viability of human embryos with an imaging system. The method includes: receiving a series of time-lapse images of a human embryo contained in a multi-well culture dish including a plurality of micro-wells; generating a first mask for a first image of the series of time-lapse images, which first mask obscures a first area; and generating a second mask for the first image of the series of time-lapse images, which second mask obscures a second area, and which second area includes the first area and an internal portion of the human embryo image.

In some embodiments the method includes: determining the first area of the first mask; and determining the second area of the second mask. In some embodiments the method includes determining the difference in between the first area and second area of the first mask and second mask respectively. In some embodiments, generating the first mask further includes: generating a preliminary mask, which preliminary mask includes a plurality of components; determining a first connected component from the plurality of components; designating the first connected component as the first mask; and eliminating the plurality components other than the first connected component from the first mask. In some embodiments, the first connected component is the largest component of the plurality of components. In some embodiments the method includes: identifying at least one hole in the first mask; and filing the identified at least one hole in the first mask.

One aspect of the present disclosure relates to an imaging system for evaluation of human embryos to determine a development potential. The imaging system includes: a stage that can receive a multi-well culture dish including a plurality of micro-wells containing a sample including at least one human embryo; a time-lapse microscope that can acquire a series of time-lapse images of the at least one human embryo contained by the multi-well culture dish on the stage, which time-lapse microscope can: select an image of the human embryo, which image includes a plurality of pixels; select a pixel from the plurality of pixels; determine features of the selected pixel by generating a plurality of random boxes of random sizes and at random locations about the selected pixel; and identify, based on the determined features, the selected pixel as one of: inside of a mask area; and outside of the mask area.

In some embodiments, the size of each of the random boxes is randomly generated within a predetermined range.

In some embodiments, the predetermined range includes a first portion specifying a range of lengths of the random boxes and a second portion specifying a range of widths of the random boxes. In some embodiments, the predetermined range specifies limits for the size of the random boxes. In some embodiments, the predetermined range specifies boxes sized from [3, 1] pixels to [3, 7] pixels.

In some embodiments, the random locations of the random boxes are randomly generated within a predetermined range of acceptable locations about the pixel. In some embodiments, the predetermined range of acceptable locations is defined by a radius extending from the pixel. In some embodiments, a length of the radius is up to 7 pixels.

In some embodiments, determining features of the selected pixel by generating the plurality of random boxes includes: identifying an image attribute for each of the generated random boxes; and pairing each of the generated random boxes with another of the generated random boxes. In some embodiments, pairing each of the generated random boxes with another of the generated random boxes includes generating 50 pairs of boxes. In some embodiments, determining features of the selected pixel by generating the plurality of random boxes further includes comparing the image attribute of the paired random boxes with each other.

In some embodiments, identifying the selected pixel as one of: inside of the mask area; and outside of the mask area, includes applying results of the comparison of the image attribute of the paired random boxes to a statistical model. In some embodiments, the results of the comparison of the image attribute of the paired random boxes are applied to the statistical model with a classifier. In some embodiments, the classifier includes one of: a Random Forest classifier; an AdaBoost classifier; a Naïve Bayes classifier; Boosting Tree, and a Support Vector Machine.

In some embodiments, the time-lapse microscope can further: iteratively select pixels from the plurality of pixels; determine features of the iteratively selected pixels by generating another plurality of random boxes of random sizes and at random locations about each the iteratively selected pixels; and identify, based on the determined features, each of the iteratively selected pixels as one of: inside of the mask area; and outside of the mask area. In some embodiments, the time-lapse microscope can further: generate a preliminary mask, which preliminary mask is generated based on a designation of pixels as one of inside of the mask area; and outside of the mask area, and which preliminary mask includes a plurality of components formed from the pixels; determine a first connected component from the plurality of components; designate the first connected component as the first mask; and eliminate the plurality components other than the first connected component from the first mask.

In some embodiments, the first connected component is the largest component of the plurality of components. In some embodiments, the time-lapse microscope can generate a final mask, which generating of the final mask can include: identifying at least one hole in the first mask; and filing the identified at least one hole in the first mask. In some embodiments, the time-lapse microscope can apply the final mask over the received image. In some embodiments, applying the final mask over the received image enables identification of at least one of: cavitation; and hatching. In some embodiments, the time-lapse microscope can further: identify portions of a multi-well culture dish well containing the human embryo that are visible in the image of the human embryo; and remove the visible portions of a multi-well culture dish well from the image of the human embryo.

One aspect of the present disclosure relates to an imaging system for evaluation of human embryos to determine a development potential. The system includes: a stage that can receive a multi-well culture dish including a plurality of micro-wells containing a sample including at least one human embryo; and a time-lapse microscope that can acquire a series of time-lapse images of the at least one human embryo contained by the multi-well culture dish on the stage. In some embodiments, the time-lapse microscope can: select an image of the human embryo from the series of time-lapse images; generate an embryo mask for the received image, which embryo mask distinguishes between an embryo image and other portions of the embryo image; detect a feature of the image based on the embryo mask; and generate a viability prediction based on the detected image based feature.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
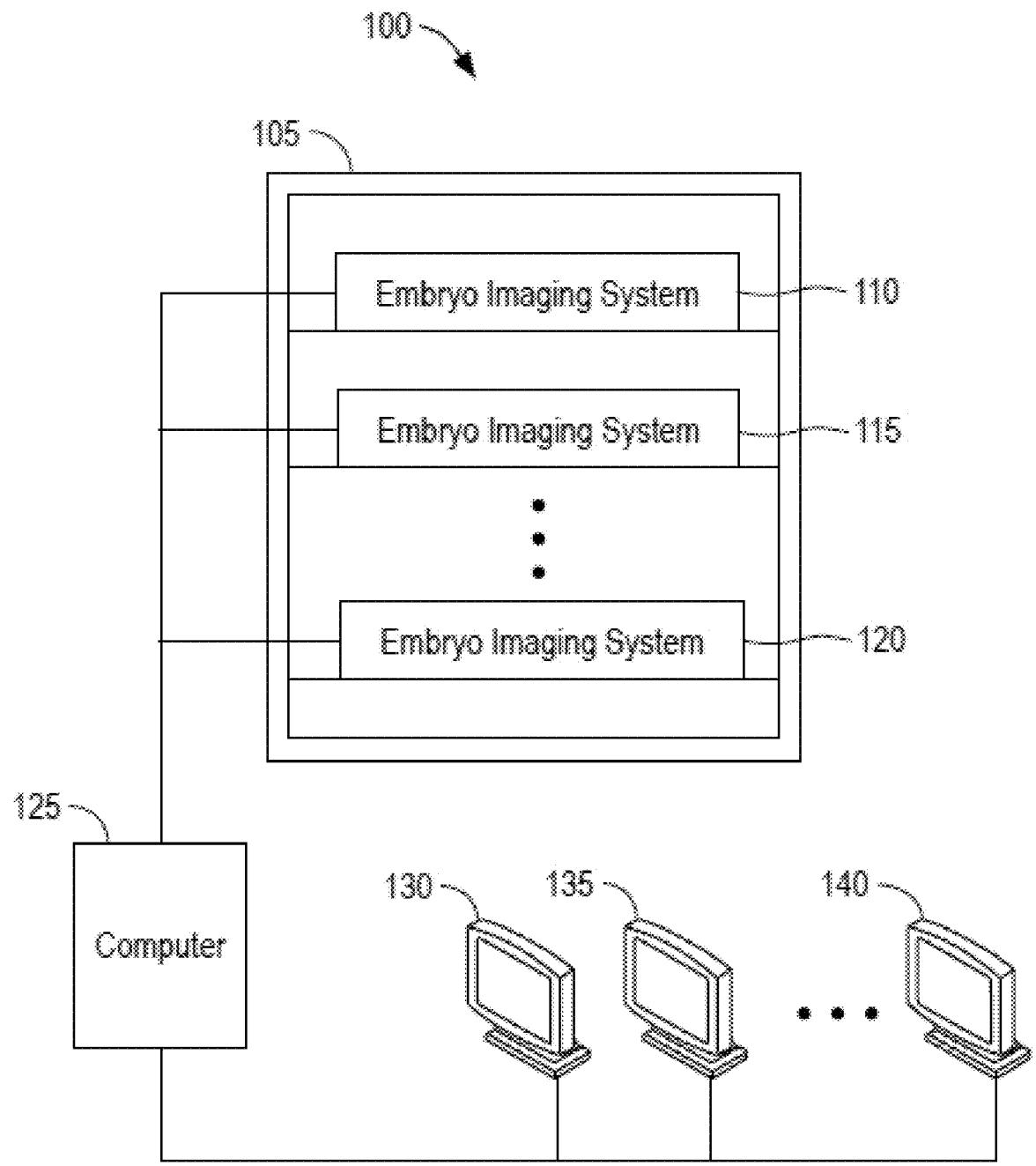
FIG. 1 illustrates a schematic diagram of an apparatus, according to an embodiment of the invention.

Before the present apparatuses, systems, and methods are described, it is to be understood that this invention is not limited to particular apparatus, system, or method described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a computer" includes a plurality of such computers known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "developmental potential" and "developmental competence" are used herein to refer to the ability or capacity of a healthy embryo or pluripotent cell to grow or develop.

The term "embryo" is used herein to refer both to the zygote that is formed when two haploid gametic cells, e.g., an unfertilized secondary oocyte and a sperm cell, unite to form a diploid totipotent cell, e.g., a fertilized ovum, and to the embryo that results from the immediately subsequent cell divisions, i.e. embryonic cleavage, up through the morula, i.e. 16-cell stage and the blastocyst stage (with differentiated trophoectoderm and inner cell mass).

The term "pluripotent cell" is used herein to mean any cell that has the ability to differentiate into multiple types of cells in an organism. Examples of pluripotent cells include stem cells oocytes, and 1-cell embryos (i.e. zygotes).

The term "stem cell" is used herein to refer to a cell or a population of cells which: (a) has the ability to self-renew, and (b) has the potential to give rise to diverse differentiated cell types. Frequently, a stem cell has the potential to give rise to multiple lineages of cells. As used herein, a stem cell may be a totipotent stem cell, e.g. a fertilized oocyte, which gives rise to all of the embryonic and extraembryonic tissues of an organism; a pluripotent stem cell, e.g. an embryonic stem (ES) cell, embryonic germ (EG) cell, or an induced pluripotent stem (iPS) cell, which gives rise to all of embryonic tissues of an organism, i.e. endoderm, mesoderm, and ectoderm lineages; a multipotent stem cell, e.g. a mesenchymal stem cell, which gives rise to at least two of the embryonic tissues of an organism, i.e. at least two of endoderm, mesoderm and ectoderm lineages, or it may be a tissue-specific stem cell, which gives rise to multiple types of differentiated cells of a particular tissue. Tissue-specific stem cells include tissue-specific embryonic cells, which give rise to the cells of a particular tissue, and somatic stem cells, which reside in adult tissues and can give rise to the cells of that tissue, e.g. neural stem cells, which give rise to all of the cells of the central nervous system, satellite cells, which give rise to skeletal muscle, and hematopoietic stem cells, which give rise to all of the cells of the hematopoietic system.

The term "oocyte" is used herein to refer to an unfertilized female germ cell, or gamete. Oocytes of the subject application may be primary oocytes, in which case they are positioned to go through or are going through meiosis I, or secondary oocytes, in which case they are positioned to go through or are going through meiosis II.

By "meiosis" it is meant the cell cycle events that result in the production of gametes. In the first meiotic cell cycle, or meiosis I, a cell's chromosomes are duplicated and partitioned into two daughter cells. These daughter cells then divide in a second meiotic cell cycle, or meiosis II, that is not accompanied by DNA synthesis, resulting in gametes with a haploid number of chromosomes.

By a "mitotic cell cycle", it is meant the events in a cell that result in the duplication of a cell's chromosomes and the division of those chromosomes and a cell's cytoplasmic matter into two daughter cells. The mitotic cell cycle is divided into two phases: interphase and mitosis. In interphase, the cell grows and replicates its DNA. In mitosis, the cell initiates and completes cell division, first partitioning its nuclear material, and then dividing its cytoplasmic material and its partitioned nuclear material (cytokinesis) into two separate cells.

By a "first mitotic cell cycle" or "cell cycle 1" it is meant the time interval from fertilization to the completion of the first cytokinesis event, i.e. the division of the fertilized oocyte into two daughter cells. In instances in which oocytes are fertilized in vitro, the time interval between the injection of human chorionic gonadotropin (HCG) (usually administered prior to oocyte retrieval) to the completion of the first cytokinesis event may be used as a surrogate time interval.

By a "second mitotic cell cycle" or "cell cycle 2" it is meant the second cell cycle event observed in an embryo, the time interval between the production of daughter cells from a fertilized oocyte by mitosis and the production of a first set of granddaughter cells from one of those daughter cells (the "leading daughter cell", or daughter cell A) by mitosis. Upon completion of cell cycle 2, the embryo consists of 3 cells. In other words, cell cycle 2 can be visually identified as the time between the embryo containing 2-cells and the embryo containing 3-cells.

By a "third mitotic cell cycle" or "cell cycle 3" it is meant the third cell cycle event observed in an embryo, typically the time interval from the production of daughter cells from a fertilized oocyte by mitosis and the production of a second set of granddaughter cells from the second daughter cell (the "lagging daughter cell" or daughter cell B) by mitosis. Upon completion of cell cycle 3, the embryo consists of 4 cells. In other words, cell cycle 3 can be visually identified as the time between the embryo containing 3-cells and the embryo containing 4-cells.

By "first cleavage event", it is meant the first division, i.e. the division of the oocyte into two daughter cells, i.e. cell cycle 1. Upon completion of the first cleavage event, the embryo consists of 2 cells.

By "second cleavage event", it is meant the second set of divisions, i.e. the division of leading daughter cell into two granddaughter cells and the division of the lagging daughter cell into two granddaughter cells. In other words, the second cleavage event consists of both cell cycle 2 and cell cycle 3. Upon completion of second cleavage, the embryo consists of 4 cells.

By "third cleavage event", it is meant the third set of divisions, i.e. the divisions of all of the granddaughter cells. Upon completion of the third cleavage event, the embryo typically consists of 8 cells.

By "cytokinesis" or "cell division" it is meant that phase of mitosis in which a cell undergoes cell division. In other words, it is the stage of mitosis in which a cell's partitioned nuclear material and its cytoplasmic material are divided to produce two daughter cells. The period of cytokinesis is identifiable as the period, or window, of time between when a constriction of the cell membrane (a "cleavage furrow") is first observed and the resolution of that constriction event, i.e. the generation of two daughter cells. The initiation of the cleavage furrow may be visually identified as the point in which the curvature of the cell membrane changes from convex (rounded outward) to concave (curved inward with a dent or indentation). The onset of cell elongation may also be used to mark the onset of cytokinesis, in which case the period of cytokinesis is defined as the period of time between the onset of cell elongation and the resolution of the cell division.

By "first cytokinesis" or "cytokinesis 1" it is meant the first cell division event after fertilization, i.e. the division of a fertilized oocyte to produce two daughter cells. First cytokinesis usually occurs about one day after fertilization.

By "second cytokinesis" or "cytokinesis 2", it is meant the second cell division event observed in an embryo, i.e. the division of a daughter cell of the fertilized oocyte (the "leading daughter cell", or daughter A) into a first set of two granddaughters.

By "third cytokinesis" or "cytokinesis 3", it is meant the third cell division event observed in an embryo, i.e. the division of the other daughter of the fertilized oocyte (the "lagging daughter cell", or daughter B) into a second set of two granddaughters.

The term "fiduciary marker" or "fiducial marker," is an object used in the field of view of an imaging system which appears in the image produced, for use as a point of reference or a measure. It may be either something placed into or on the imaging subject, or a mark or set of marks in the reticle of an optical instrument.

The term "micro-well" refers to a container that is sized on a cellular scale, such as to provide for accommodating one or more eukaryotic cells.

Description of Disclosed Embodiments

Referring to FIG. 1, a schematic diagram of an apparatus 100 according to an embodiment of the invention is described. The apparatus 100 includes a standard incubator 105 with one or more shelves for holding imaging systems 110-120, described in more detail hereinbelow. The imaging systems 110-120 have loading platforms and are placed inside the incubator 105 to image one or more embryos cultured in dishes mounted on their loading platforms.

The imaging systems 110-120 can be coupled to a computer 125, which may be mounted on or near the incubator 105. The computer 125 includes software for analyzing the images acquired by the imaging systems 110-120. In one embodiment, the computer 125 includes software for determining the developmental potential and/or the presence of chromosomal abnormalities in cultured embryos. The computer 125 is coupled to one or more output devices that can include one or several displays or touch-screen panels, e.g., touch-screen panels 130-140. The touch-screen panels 130-140 may be configured to enable users to control the operation of the imaging systems 110-120 with an easy-to-use graphical user interface ("GUI"). In one embodiment, multiple imaging systems, e.g., the systems 110-120, may be controlled from a single touch-screen panel, and multiple touch-screen panels may be controlled from a single computer, e.g., the computer 125.

Figure 2:
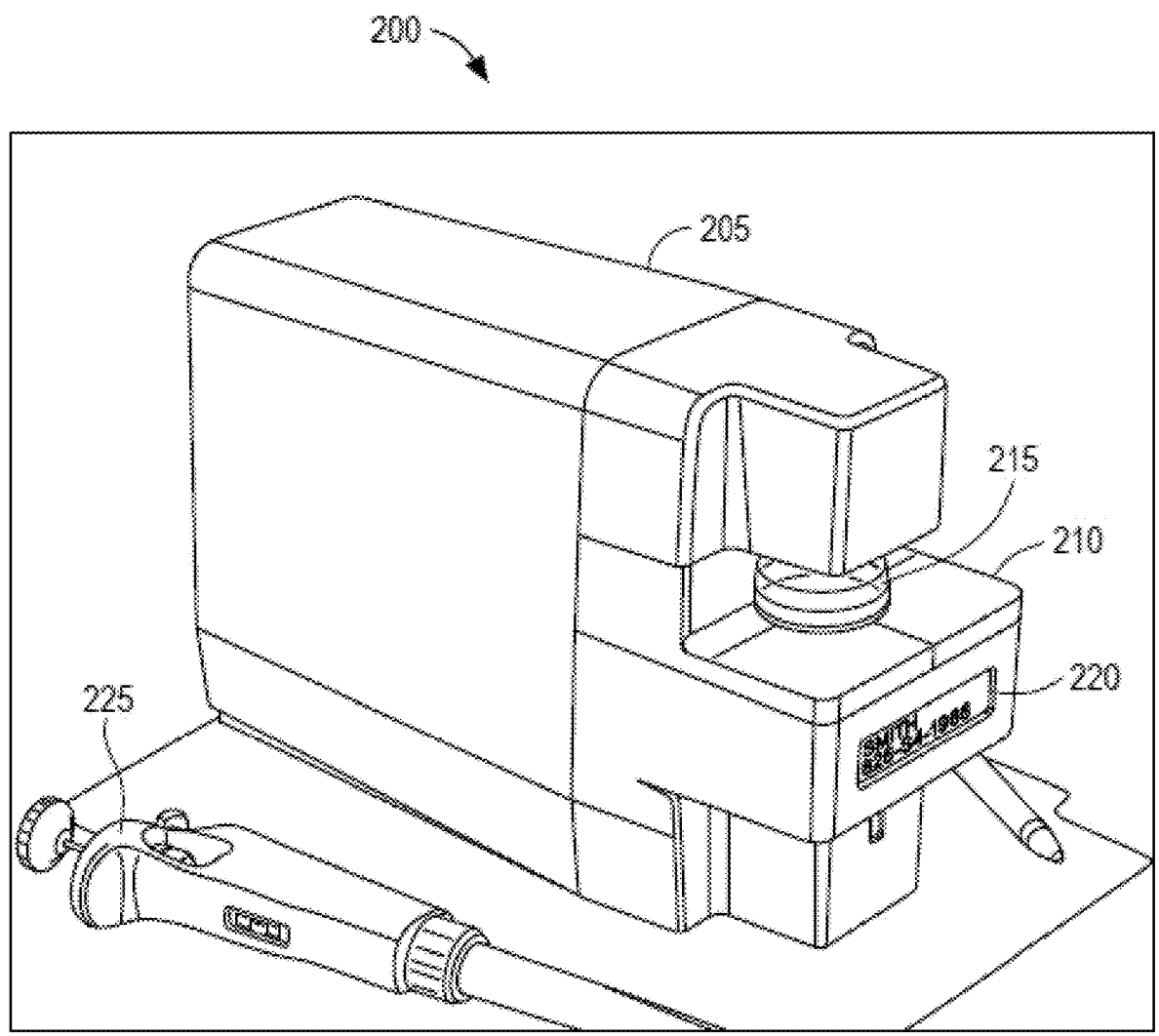
FIG. 2 illustrates a schematic diagram of an imaging system, according to an embodiment of the invention.

A schematic diagram of an imaging system 200 according to an embodiment of the invention is illustrated in FIG. 2. The imaging system 200 includes a single-channel or multi-channel microscope system including on-board electronics placed inside an outer housing 205. Referring to FIGS. 1 and 2, in one embodiment, the imaging system 200 may communicate with the computer 125. Alternatively, the imaging system 200 may communicate with a controller outside of the incubator 105 (see description with reference to FIG. 32) and may include a reduced set of on-board electronics. The remainder of the on-board electronics may be included in the controller. Housing 205 may be constructed of non-embryo-toxic materials, such as aluminum and plastics. In one embodiment, a loading platform 210, also referred to herein as the stage, extending outward from the housing 205 allows for a multi-well culture dish 215 to be positioned for imaging by the microscope system. Alternatively, the multi-well culture dish 215 may be loaded in a culture chamber integrated in the housing 205 (see description with reference to FIG. 35). Embryos may be placed in dish 215 with pipette 225. In one embodiment, the microscope system includes software to monitor the loading of a dish 215 into loading platform 210 and make any adjustments necessary for the proper imaging of the embryos cultured in the dish.

It is appreciated that a single channel/microscope system may be used to image embryos for a single patient. It is also appreciated that imaging system 200 may be built as a single-channel microscope system as illustrated in FIG. 2, or it may be built as an integrated multi-channel microscope system. Accordingly, to facilitate the monitoring of embryos inside the incubator, a LCD display 220 may be placed outside the housing 205 for showing the patient name, ID number, and other patient information to help users identify which channel is assigned to each patient. Alternatively, a color code system or other identification mechanism may also be used to identify patients.

Figure 3:
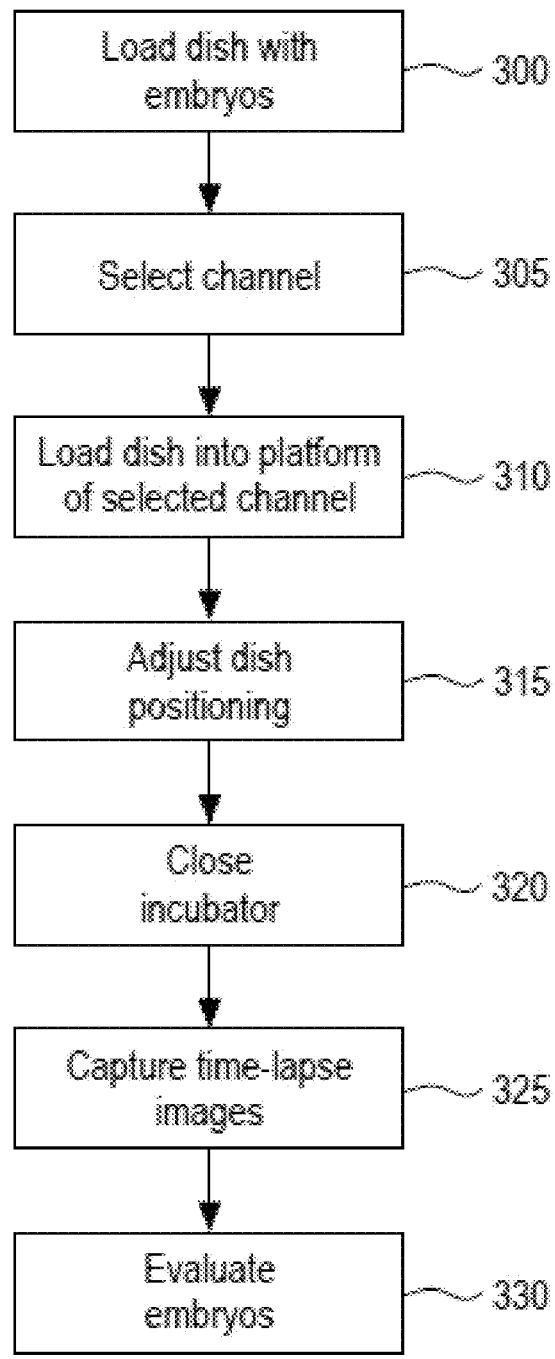
FIG. 3 illustrates a flow chart for operating an imaging system, according to an embodiment of the invention.

FIG. 3 illustrates a flow chart for operating an imaging system, according to an embodiment of the invention. The imaging system may be the imaging system 200 of FIG. 2, or other types of devices for imaging of embryos, oocytes, or pluripotent cells. A user loads a multi-well dish (such as the multi-well dish 215 of FIG. 2, the multi-well dish 900 of FIG. 9, or the multi-well dish 930 of FIG. 9C) with one or more embryos into loading platform 210 (300). Using a GUI on one of the touch-screen panels 130-140, the user selects a microscope channel in an imaging system to image the embryos (305). In doing so, the user inputs patient information (e.g., name, ID) in the GUI to facilitate patient's identification. The patient information can also be entered automatically using a bar-code scanner or other means. For example, a separate device such as a hand-held scanner could be used a priori to scan the bar-code on a multi-well dish. Then, when the dish is loaded into the imaging system 200, the bar-code can be scanned again (e.g., via a scanner built in to the imaging system or its platform) to identify the patient identification. The patient information can be displayed on an LCD screen on the imaging system, on the touch-screen panel outside the incubator, and elsewhere.

The multi-well dish can be placed on the loading platform of the selected channel in a given position and orientation (310), which may be adjusted by a software in the selected channel to ensure proper imaging of the embryos in the multi-well dish (315). In one embodiment, the software recognizes when the multi-well dish is loaded properly and alerts the user of its proper loading by a light emitting diode (LED) indicator or other alert mechanism. In addition, the dish may have a keying feature that allows loading of the dish in a single possible position and orientation.

After closing of the incubator door (320), the time-lapse imaging capture of the embryos can be initialized by first performing auto-focus and auto-exposure and verifying the quality of the acquired images (325). In one embodiment, images may be acquired at every given interval for a number of days. For example, images may be acquired every 1, 2, 3, 4, 5, 6, 7, 8, 9, 10, 15, 20, 25, or 30 minutes for 6 hours, 12 hours, 1 day, 2 days, 3 days, 4 days, 5 days, 6 days, 1 week, 2 weeks or 3 weeks.

Lastly, software in the selected channel and/or the computer 125 analyzes the captured images and measures predictive parameters to provide a prediction of which embryos will reach blastocyst and/or a ranking of embryo quality. The prediction can be provided to the user via the GUI and the output device. The prediction enables the user to determine which embryos have development potential for human implantation.

Figure 4:
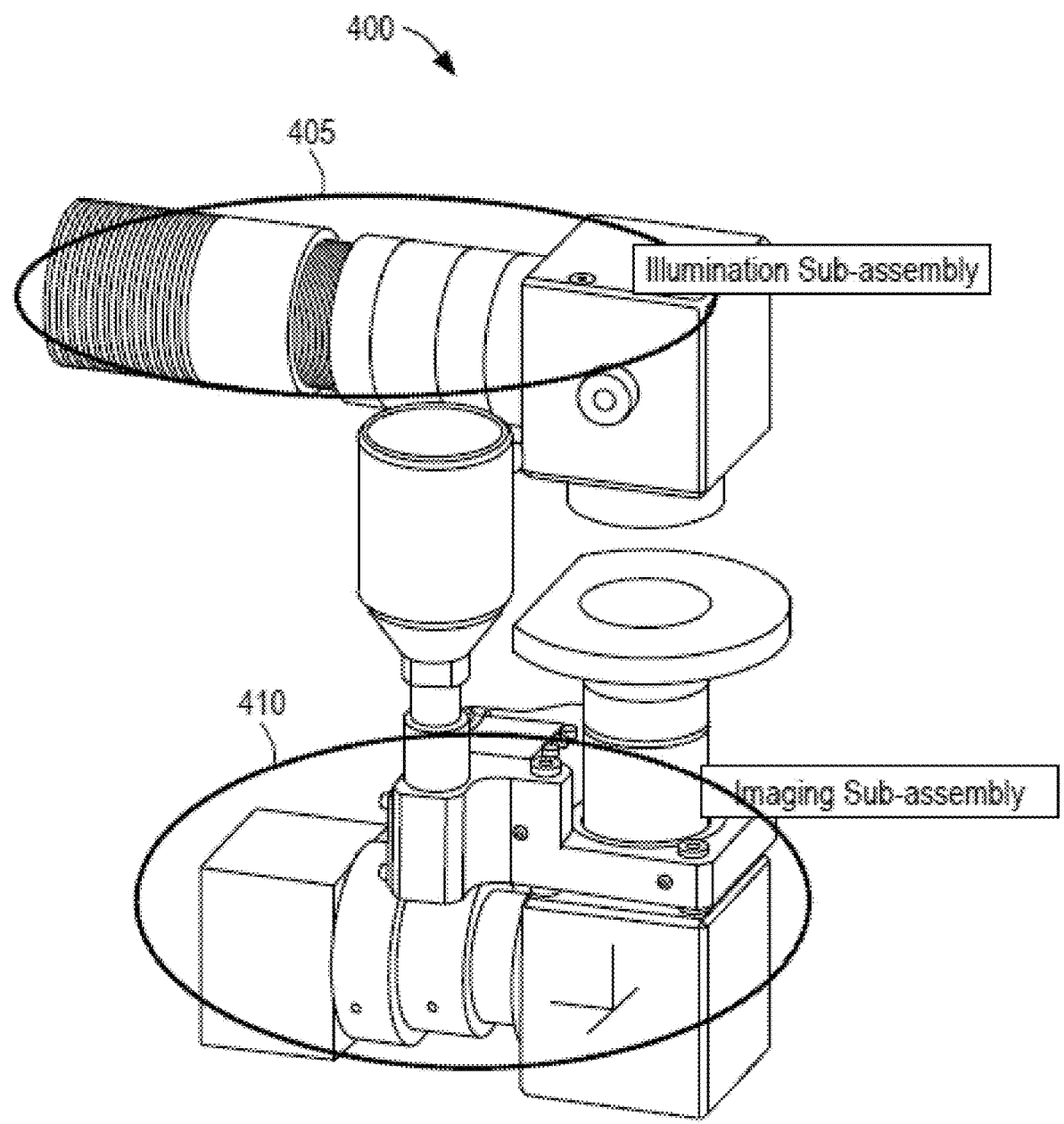
FIG. 4 illustrates a schematic diagram of a microscope placed inside an imaging system, according to an embodiment of the invention.

Referring now to FIG. 4, a schematic diagram of a microscope 400 placed inside an imaging system is described, according to an embodiment of the invention. The microscope 400 may be used with the imaging system 200 of FIG. 2, or other types of devices for imaging of embryos, oocytes, or pluripotent cells. The microscope 400 may be any computer-controlled microscope that is equipped for digital image storage and analysis. In one embodiment, the microscope 400 includes an illumination sub-assembly 405 and an imaging sub-assembly 410. In one embodiment, the illumination sub-assembly 405 provides darkfield illumination and may include a red LED, a collimating lens, a diffuser, a darkfield aperture, a right-angle mirror, and a condenser lens, among other optical components.

Imaging sub-assembly 410 may include an imaging objective lens (10×), a stage such as a translation stage to focus the objective lens, a motor coupled to the translation stage to provide computer-controlled focus, a right-angle mirror, a 4× objective lens that acts as a high-quality tube lens, and a CMOS camera to capture images. It is appreciated that the field of view is large enough to view a set of micro-wells. It is also appreciated that some embodiments may use a light having a color other than red, a CCD camera, and different field of view, depth of field, optical layout, magnification objectives (e.g., 20×, 40×, etc.), motor, a positioning mechanism for moving a group of micro-wells under the field-of-view, and so on.

It is further appreciated that the microscope 400 may employ brightfield illumination, oblique brightfield, darkfield illumination, phase contrast, Hoffman modulation contrast, differential interference contrast, or fluorescence. In some embodiments, darkfield illumination may be used to provide enhanced image contrast for subsequent feature extraction and image analysis. Darkfield illumination can also be achieved using epi-illumination, where the illumination light comes up through the imaging objective and illuminates the sample from beneath, rather than from above.

Figure 5A:
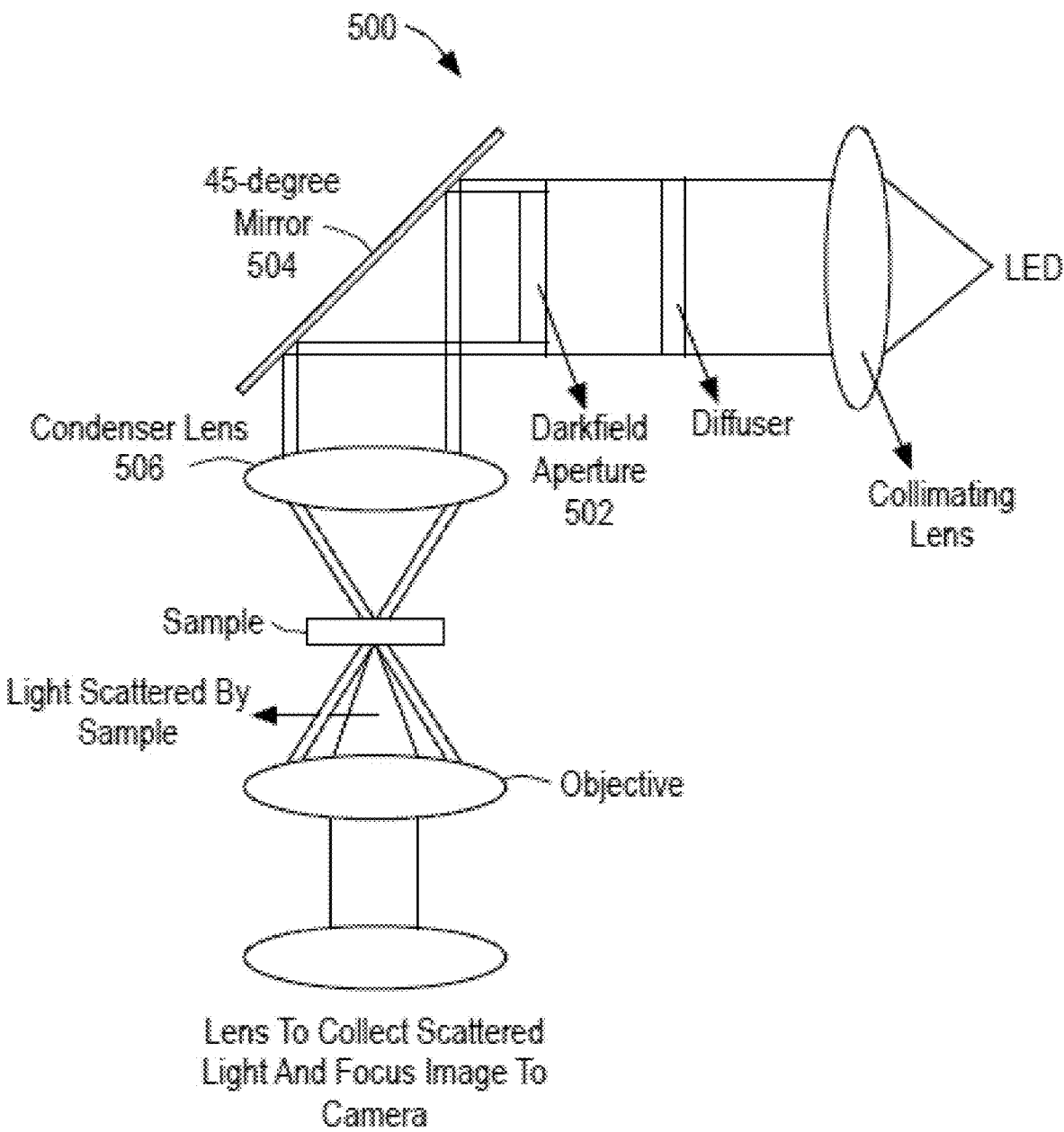
FIGS. 5A-D illustrate schematic views of examples of darkfield illumination systems that may be used by the microscope of FIG. 4, according to an embodiment of the invention.
Figure 5B:
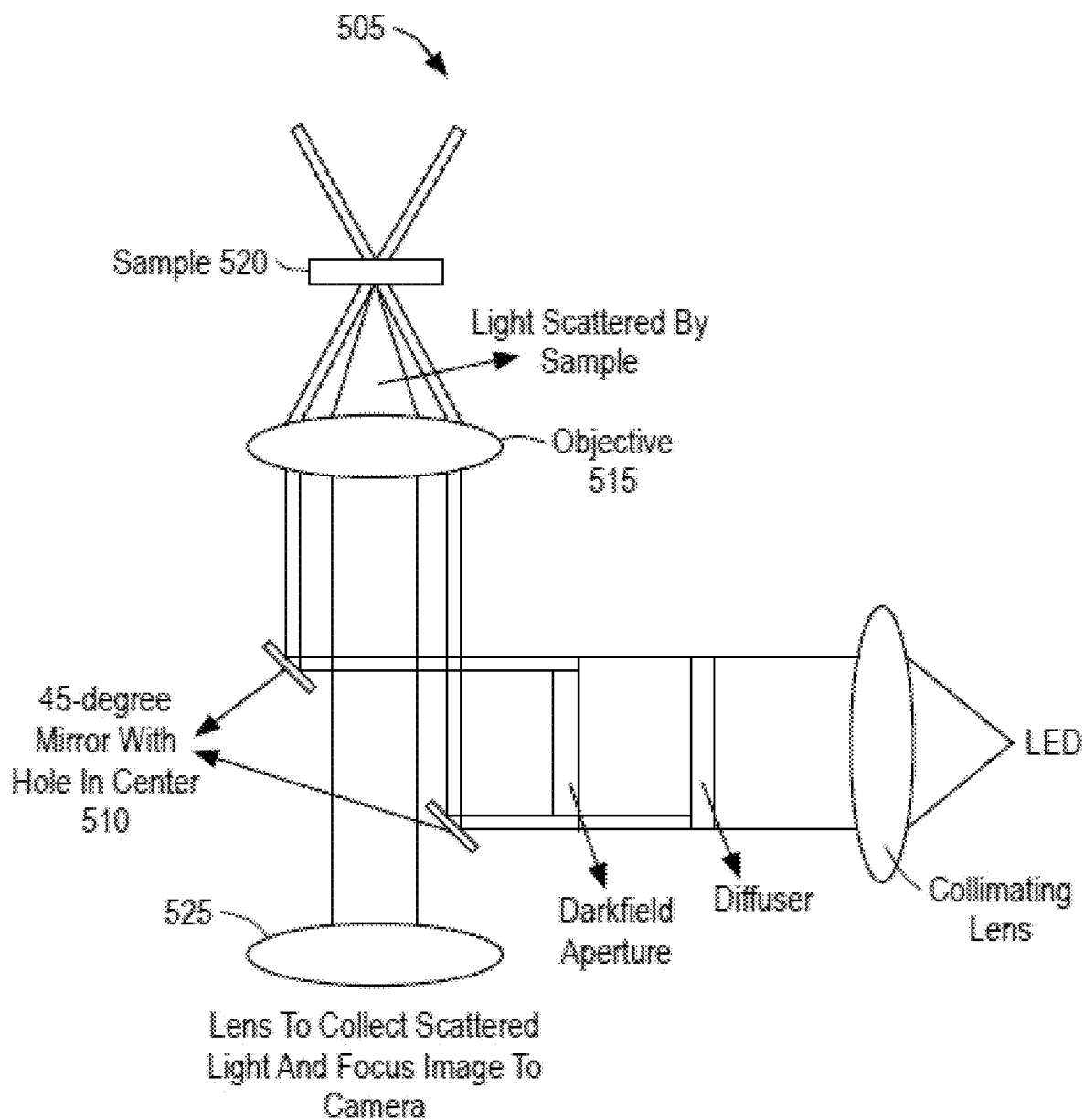
Figure 5C:
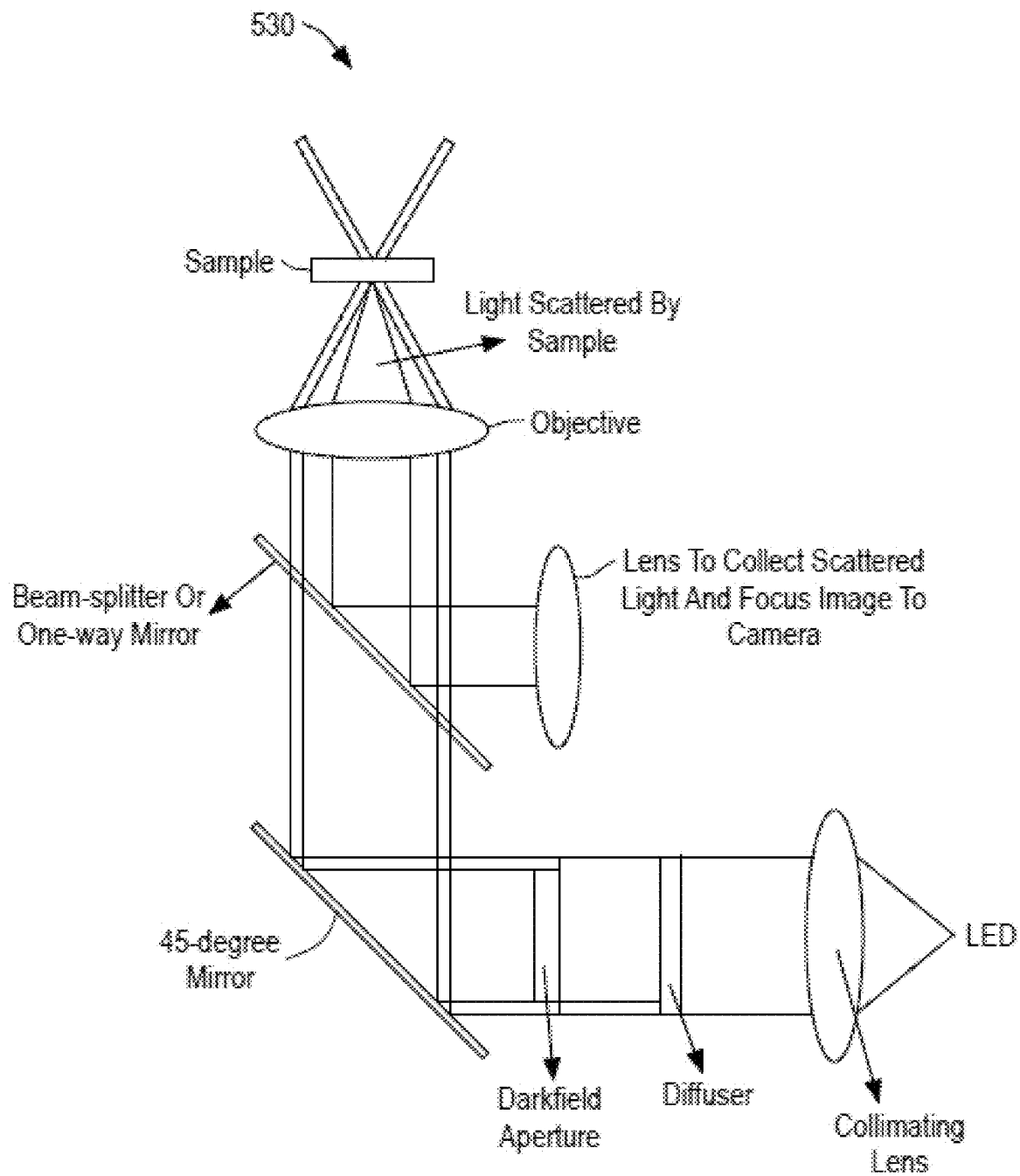

FIGS. 5A-C illustrate schematic views of examples of darkfield illumination systems that may be used by the microscope 400 of FIG. 4, according to an embodiment of the invention. Darkfield illumination system 500 of FIG. 5A illustrates an example of a traditional darkfield illumination approach for use with time-lapse microscopes such as the microscope 400, darkfield illumination system 505 of FIG. 5B illustrates an example of an approach using epi-illumination, and darkfield illumination system 530 of FIG. 5C illustrates another approach for epi-illuminated darkfield. In system 505, for example, a 45-degree mirror 510 with a circular hole in the middle can be placed under the imaging objective 515. A hollow cone of light is reflected off the mirror and up towards the imaging objective 515, where it gets focused to the sample 520. Light scattered by the sample 520 gets collected by the same imaging objective 515 and passes through the hole in the mirror 510 and towards a tube-lens and camera 525 for collecting the image. In addition, red or near-infrared light sources may be used to reduce phototoxicity and improve the contrast ratio between cell membranes and the inner portion of the cells. In other embodiments, images can be captured using one or more illumination wavelengths and the various images can be combined or used to provide additional information.

In one embodiment, a darkfield aperture 502 illustrated in FIG. 5A may be placed as shown. Alternatively, the darkfield aperture 502 may be placed in other configurations, such as between the 45-degree mirror 504 and the condenser lens 506, or after the condenser lens 506.

Images that are acquired by the microscope 400 may be stored either on a continuous basis, as in live video, or on an intermittent basis, as in time lapse photography, where a subject is repeatedly imaged in a still picture. In one embodiment, the time interval between images is between 1 to 30 minutes in order to capture significant morphological events as described below. In an alternative embodiment, the time interval between images can be varied depending on the amount of cell activity.

For example, during active periods images could be taken as often as every few seconds or every minute, while during inactive periods images could be taken every 10 or 15 minutes or longer. Real-time image analysis on the captured images could be used to detect when and how to vary the time intervals. It is appreciated that the light intensity for a time-lapse imaging system may be significantly lower than the light intensity typically used on an assisted reproduction microscope due to the low-power of the LEDs (for example, using a 1 W red LED compared to a typical 100 W Halogen bulb) and high sensitivity of the camera sensor. Thus, the total amount of light energy received by an embryo using the microscope 400 is comparable to or less than the amount of energy received during routine handling at an IVF clinic. For example, for 2 days of imaging, with images captured every 5 minutes at 0.5 seconds of light exposure per image, the total amount of low-level light exposure can be equivalent to roughly 30 seconds of exposure under a typical IVF inverted microscope.

Following image acquisition, the images are extracted and analyzed for different cellular parameters related to embryo, stem cell, and/or oocyte development, for example, cell size, thickness of the zona pellucida, degree of fragmentation, particle motion in the cytoplasm, symmetry of daughter cells resulting from a cell division, duration of first cytokinesis, time interval between cytokinesis 1 and cytokinesis 2, time interval between cytokinesis 2 and cytokinesis 3, and time intervals and durations of the first and second polar body extrusions.

Figure 5D:
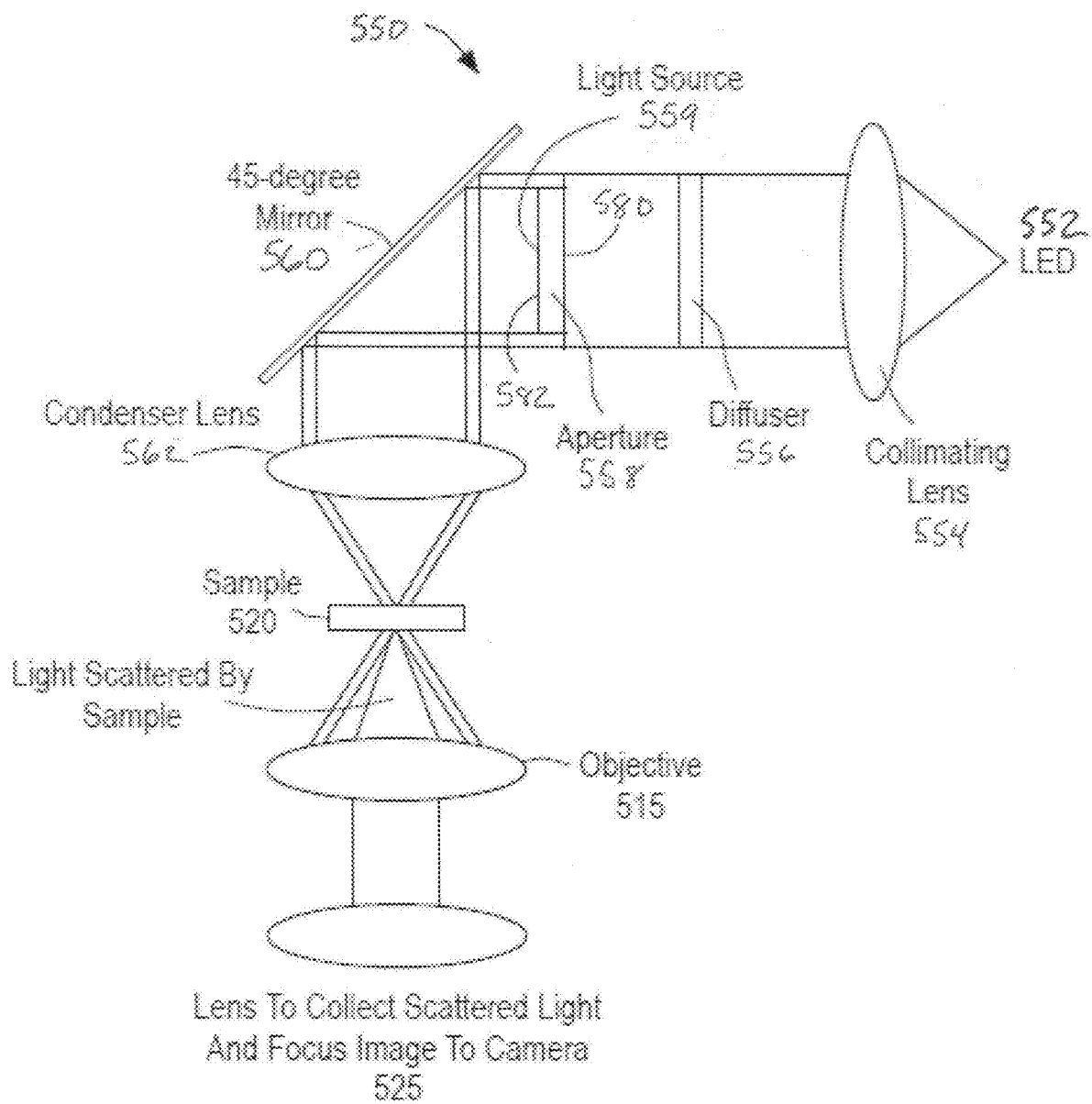

FIG. 5D illustrates a schematic view of bimodal illumination that may be used by the microscope 400 of FIG. 4, according to one embodiment of the invention. In one embodiment, an illumination assembly 550 may include a first light source 552, an aperture 558, a second light source 559, and a condenser lens 562, among other optical components. In one embodiment, the first light source 552 and the second light source 559 may be red LEDs. In one embodiment, the aperture 558 may be a darkfield aperture having a first surface 580 configured to block light and a second surface 582 opposite to the first surface 580. The aperture 558 may define at least one opening 592 through which the hollow cone of light can pass. The second light source 559 may be attached to the second surface 582 of the aperture 558.

In a first mode of the illumination assembly 550, the first light source 552 generates light that traverses a collimating lens 554, the at least one opening 592 in the aperture 558 and the condenser lens 562 prior to reaching the sample 520. The aperture 558 may be placed before or after the condenser lens 562. The light may also traverse a diffuser 556. The light that passes through the at least one opening 592 may be reflected by the 45-degree mirror 560. In one embodiment, a hollow cone of light passes through the at least one opening 592 in the aperture 558, while the remainder of the light is blocked by the aperture 558. In the first mode, the second light source 559 does not generate light. Light scattered by the sample 520 then traverses the imaging objective 515 and the tube-lens and camera 525 for collecting the image. As described, in the first mode of the illumination assembly 550, the illumination assembly 550 performs darkfield imaging.

In one embodiment, the aperture 558 illustrated in FIG. 5D may be placed as shown. Alternatively, the aperture 558 may be placed in other configurations, such as between the 45-degree mirror 560 and the condenser lens 562, or after the condenser lens 562.

In a second mode of the illumination assembly 550, the first light source 552 does not generate light. Instead, the second light source 559 generates light that reaches the sample 520 without traversing the at least one opening 592 in the aperture 558, such that light generated by the second light source 559 is not blocked by the aperture 558. As described, in the second mode of the illumination assembly 550, the illumination assembly 550 performs brightfield imaging.

In one embodiment, the illumination assembly 550 is configured in the first mode to perform time-lapse darkfield imaging of at least one of a human embryo, an oocyte, or a pluripotent cell. After completion of the time-lapse darkfield imaging, the illumination assembly can be configured in the second mode to perform brightfield imaging of the at least one of a human embryo, an oocyte, or a pluripotent cell. The brightfield imaging may be for intermittent image capture to enable morphological observation. For example, the illumination assembly 550 may be configured in the first mode for at least two days (and possibly a third day), and then may be configured in the second mode sometime during the third day. In this way, darkfield imaging can be performed (in the first mode) of a human embryo for at least the first two days after fertilization to minimize exposure of the embryo to light. A single brightfield image may be captured (in the second mode) sometime on the third day after fertilization. This brightfield image can facilitate morphology-based grading of the human embryo by an embryologist. By including the aperture 558 and the attached light source 559 and controlling the light sources 552 and 559 in the first mode and the second mode, the illumination assembly 550 supports both darkfield imaging and brightfield imaging in the same hardware assembly, without any mechanical moving parts. In addition, the brightfield image for grading by the embryologist can be obtained by the illumination assembly 550 without moving a dish containing the embryo. This is advantageous because the embryo may be sensitive to disturbances such as movement.

In one embodiment, the illumination assembly 550 alternates between being configured in the first mode and in the second mode at least once per hour. For example, the illumination assembly can take a darkfield image in the first mode, followed by a brightfield image in the second mode. This can be repeated periodically, such as every 5 minutes, to obtain time-lapse movies of a human embryo in both darkfield and brightfield modalities.

Figure 6:
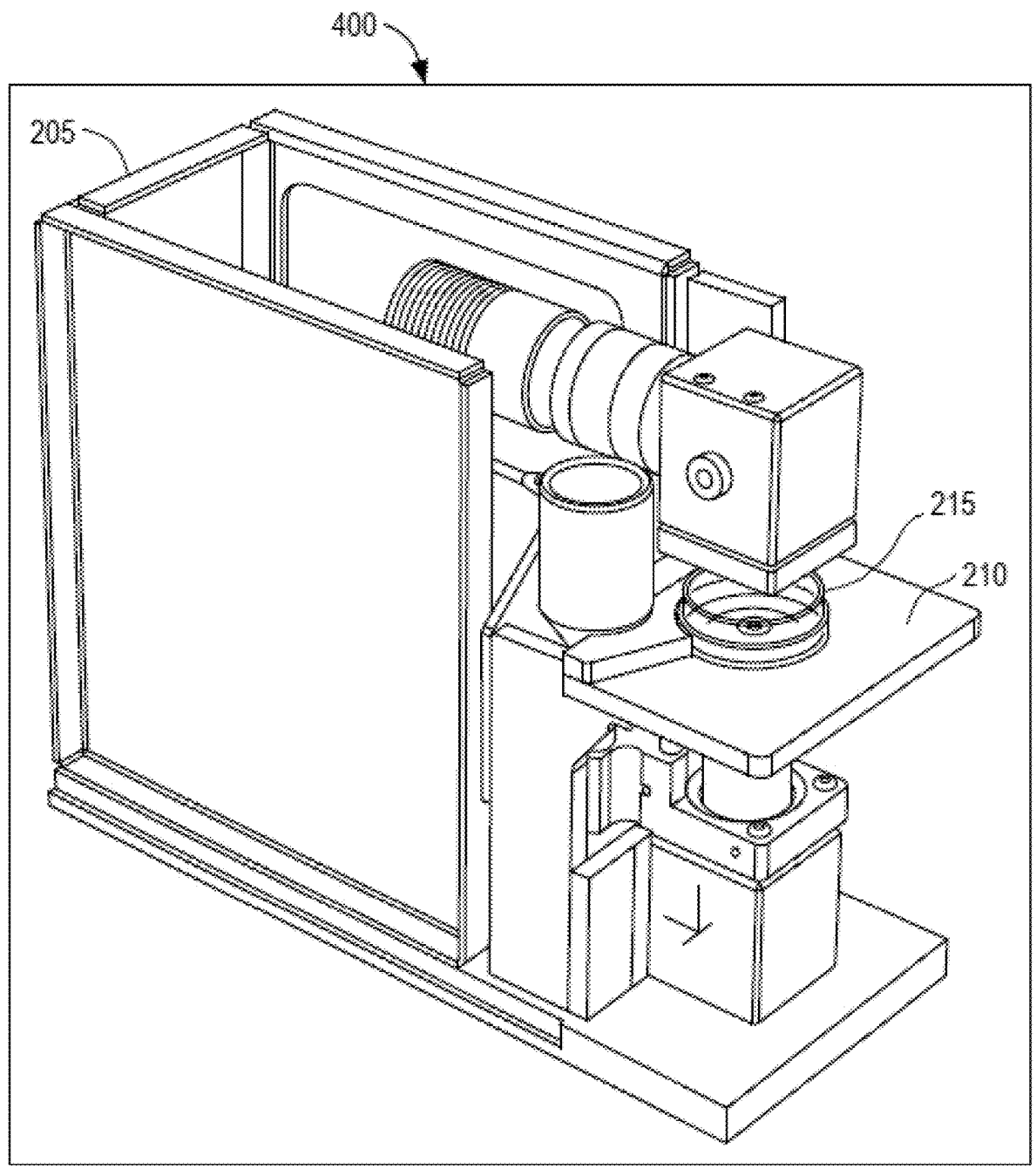
FIG. 6 illustrates a schematic view of the microscope in FIG. 4 mounted inside the housing of the imaging system of FIG. 2, according to an embodiment of the invention.

FIG. 6 illustrates a schematic view of the microscope 400 of FIG. 4 mounted inside the housing 205 of the imaging system 200 of FIG. 2, according to an embodiment of the invention. The illumination and imaging sub-assemblies 405-410 are mounted to an aluminum (or other material) chassis (i.e., part of housing 205) that holds everything together. The chassis also mounts the loading platform 210 for the dish 215.

Figure 7:
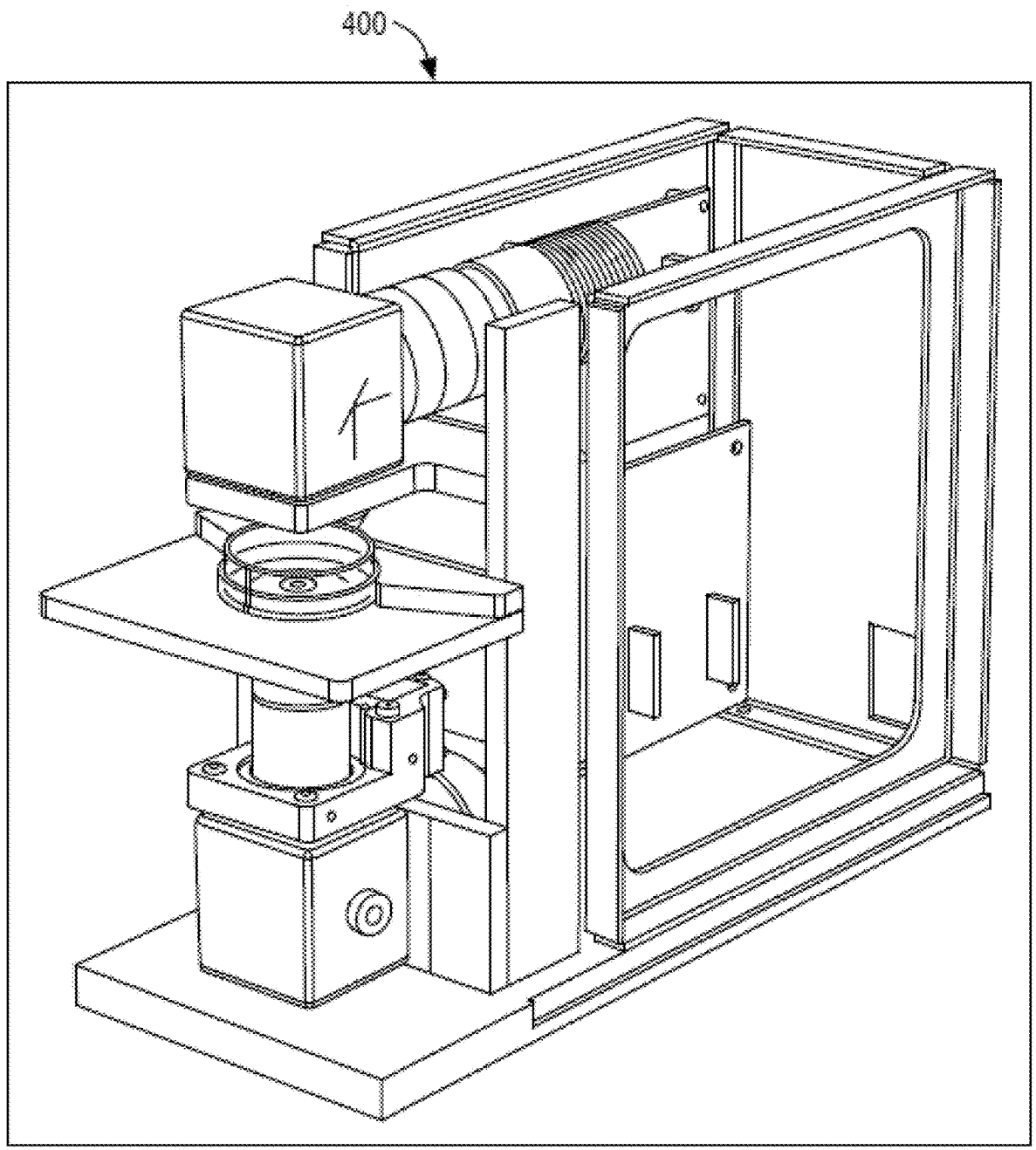
FIG. 7 illustrates a schematic view of the microscope in FIG. 4 mounted inside the housing of the imaging system of FIG. 2, according to an embodiment of the invention.

Another schematic view of the microscope inside the housing 205 is shown in FIG. 7, according to an embodiment of the invention. In this embodiment, at the back end of the microscope are the on-board electronics for controlling the motor, camera, LED, LCD display, and any other parts such as indicator LEDs. Alternatively, as described with reference to FIG. 32, all or part of the on-board electronics for controlling the motor, camera, LED, LCD display, and any other parts such as indicator LEDs may be included in a controller outside of the housing 205.

Figure 8:
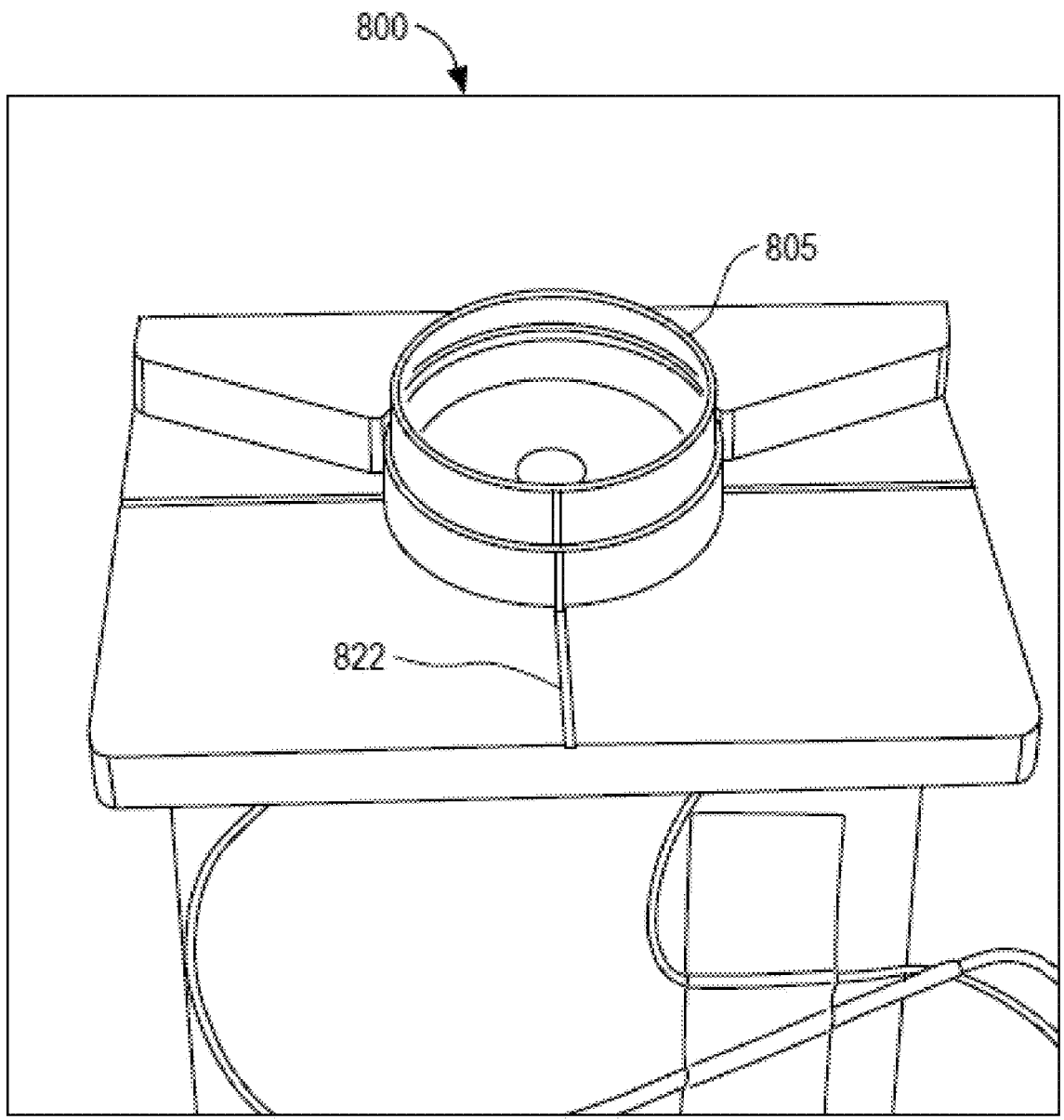
FIG. 8 illustrates a schematic diagram of a loading platform in the imaging system of FIG. 2, according to an embodiment of the invention.

Referring now to FIG. 8, a schematic diagram of a loading platform included in the imaging system 200 of FIG. 2 is described, according to an embodiment of the invention. The loading platform 800 may have several associated features to help identify if the dish 805 is located and oriented properly, such as, for example:

a back-plate to help position the dish 805;

a recessed groove (less than a millimeter deep) that the dish 805 seats into;

a keying (mechanical) feature on the dish 805 that only allows loading with one possible orientation;

markers (such as cross-hairs) to help with orientation. The user can rotate the dish 805 to align the vertical bar on the dish 805 with the central line;

an indicator LED to help illuminate the vertical bar or other feature on the dish 805;

fiducials on the dish, such as letters, numbers, dots, or lines that can be identified using the microscope and software;

software that uses the microscope to capture images of the dish 805 and monitor the loading procedure. An indicator LED could change colors to alert the user when the dish 805 is oriented correctly or incorrectly; and/or software that can account for misalignments (and potentially allow loading with an arbitrary orientation) and adjust the image accordingly.

It is appreciated that other mechanical and electronic components may be included in loading platform 800 for securing dish 805 into place.

Figure 9A:
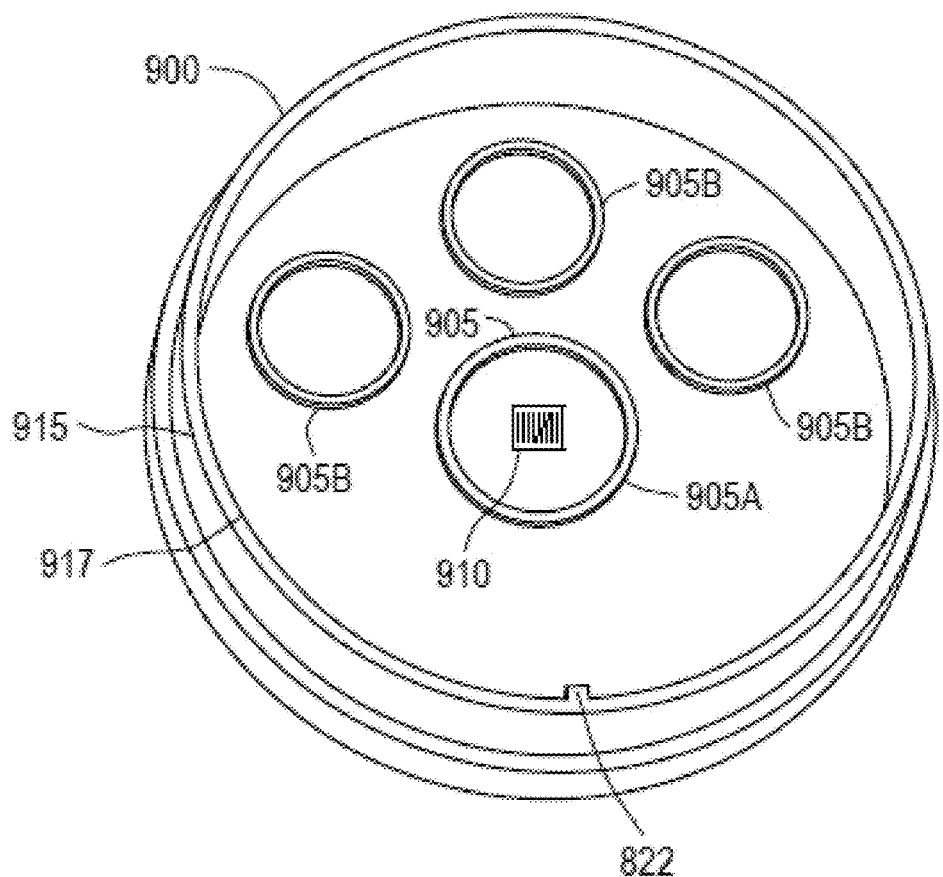
FIGS. 9A-F illustrate a schematic diagram of a multi-well culture dish, according to an embodiment of the invention.
Figure 9B:
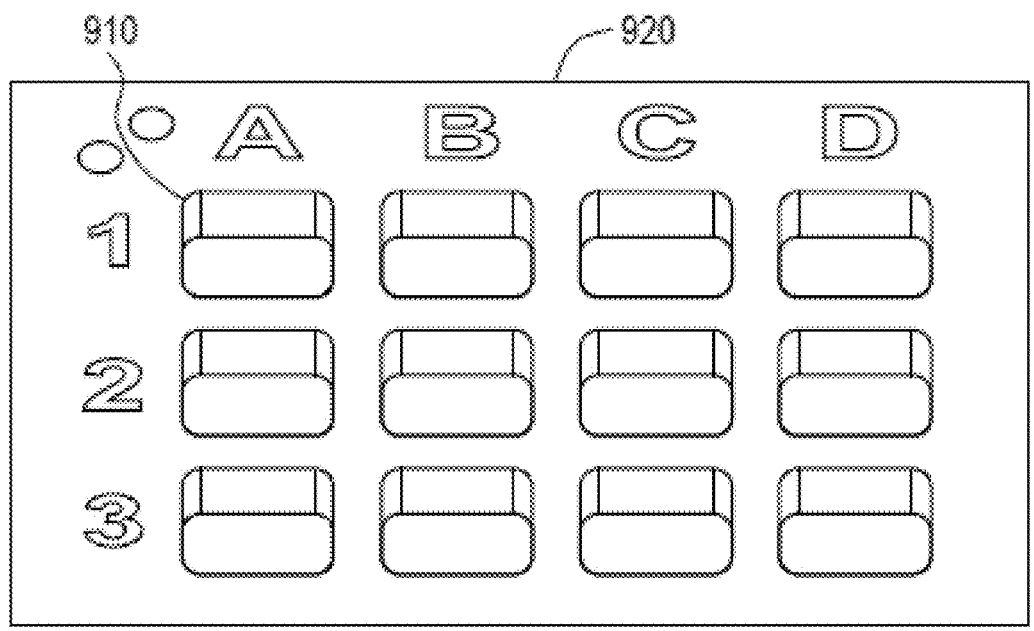

FIGS. 9A-B illustrate schematic diagrams of a multi-well culture dish 900, according to an embodiment of the invention. The dish 900 may be used with the imaging apparatus 200 of FIG. 2 or other types of devices for imaging of embryos, oocytes, or pluripotent cells. The dish 900 may include multiple rings 905. In one embodiment, the rings 905 may be substantially circular. Alternatively, the rings 905 may be oblong. One of the rings 905A may substantially circumscribe one or more wells 910. The ring 905A may be substantially centrally disposed in the dish 900. The wells 910 may be micro-wells. In one embodiment, each micro-well 910 can hold a single embryo, oocyte, or pluripotent cell, and the bottom surface of each micro-well 910 can have an optical quality finish such that a group of embryos within a single group of micro-wells can be imaged simultaneously by a single miniature microscope with sufficient resolution to follow cellular events. Each micro-well 910 may also be designed with a depth to facilitate its use. In one embodiment, the dish 900 may include one or more rings 905B. The rings 905B may be laterally offset from the ring 905A, and may be used to hold media drops for rinsing.

Referring to FIG. 9A, in one embodiment, an outer ring 915 may be positioned around the rings 905. The marker 822 (described with reference to FIG. 8) may be disposed adjacent to a lateral surface 917 of the outer ring 915.

Referring to FIG. 9B, in one embodiment, the micro-wells 910 may be disposed in a grid 920, such as a rectangular grid or a square grid. For example, the grid 920 may be 3×4 (as shown in FIG. 9B), 3×3, or 4×5. However, the dimensions of the grid are not limited to these examples.

Figure 9C:
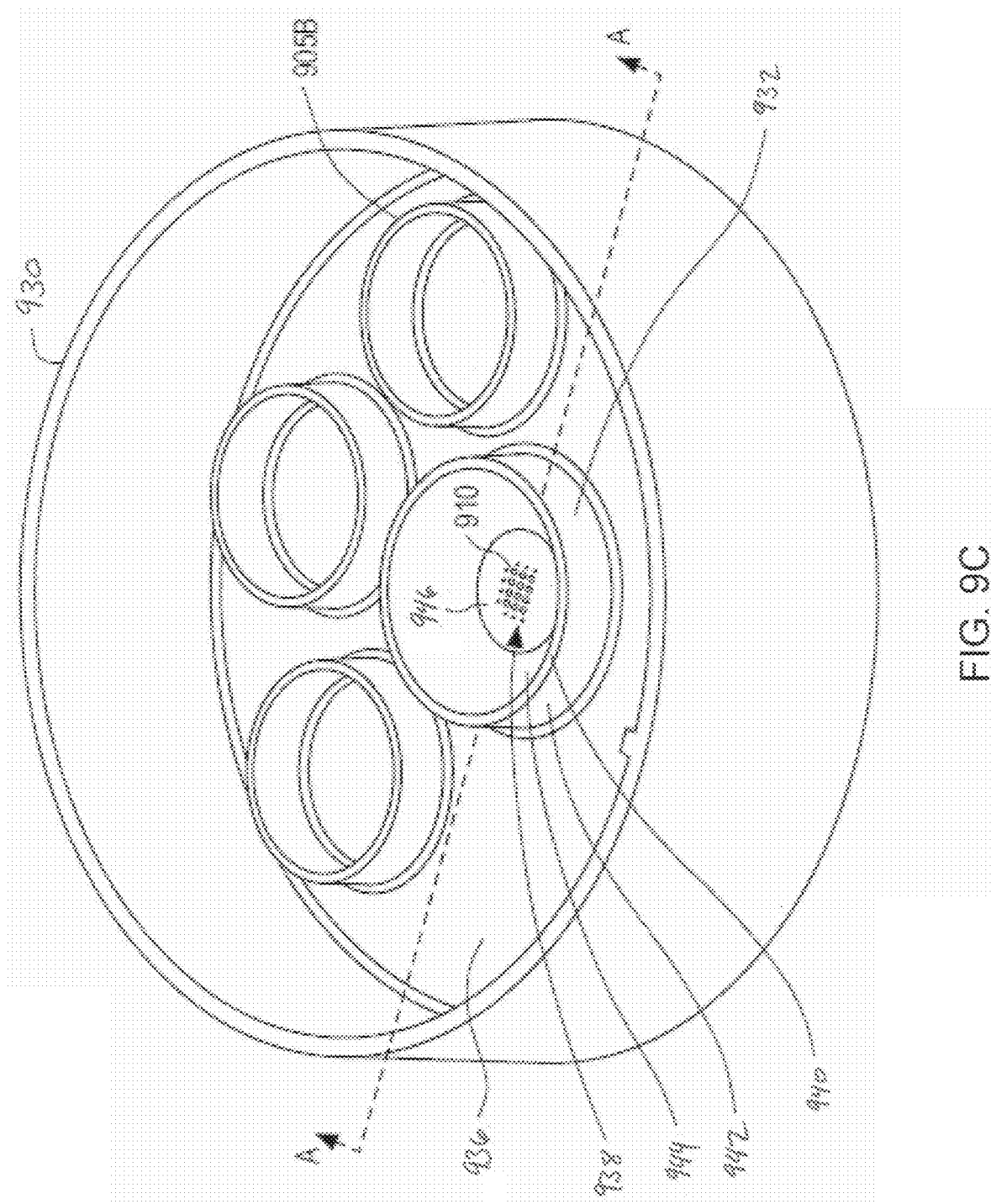

FIG. 9C illustrates a schematic diagram of a multi-well culture dish 930, according to an embodiment of the invention. The dish 930 may be used with the imaging apparatus 200 of FIG. 2, or other types of devices for imaging of embryos, oocytes, or pluripotent cells. The dish 930 may include a ring 932 that may be substantially centrally disposed in the dish 930. In one embodiment, the ring 932 may be substantially circular. Alternatively, the ring 932 may be oblong. The ring 932 may substantially circumscribe one or more wells 910 (described with reference to FIGS. 9A and 9B). The dish 930 may also include one or more rings 905B (described with reference to FIGS. 9A and 9B).

Figure 9D:
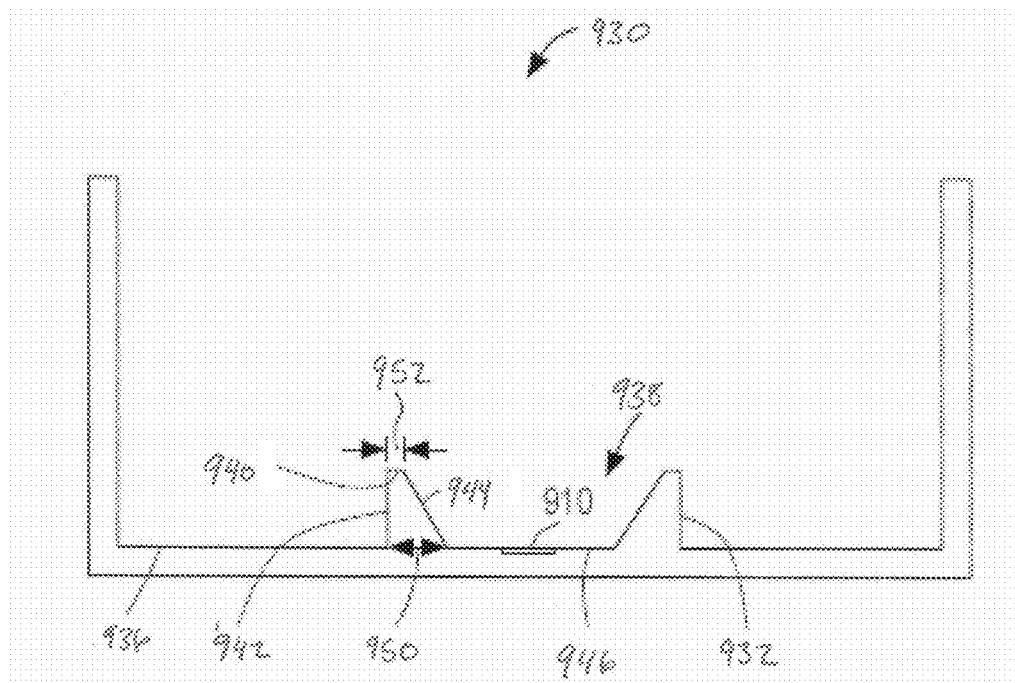

FIG. 9D illustrates a cross-section view of the multi-well culture dish 930 along cross-section A-A in FIG. 9C, according to an embodiment of the invention. Referring to FIGS. 9C and 9D, the ring 932 is disposed on a lower surface 936 of the dish 930. The ring 932 defines a cavity 938, and has an upper surface 940, an outer lateral surface 942, and an inner lateral surface 944. The cavity 938 has a cavity bottom 946, and the micro-wells 910 are defined by the cavity bottom 946. The inner lateral surface 944 of the ring 932 is disposed between the outer lateral surface 942 and the micro-wells 910, and extends from the upper surface 940 of the ring 932 to the cavity bottom 946.

In one embodiment, the inner lateral surface 944 slopes toward the micro-wells 910 such that a first width 950 of the ring 932 at the lower surface 936 of the dish 930 is greater than a second width 952 of the ring 932 at the upper surface 940 of the ring 932. In one embodiment, the first width 950 is in the range from about two times to about six times as large as the second width 952, such as three times, four times, or five times as large. Alternatively, the inner lateral surface 944 may be substantially vertical, such that the first width 950 is approximately equal to the second width 952.

Movement of a media drop stored in the ring 932 may be caused by movement of the dish 930, such as due to transport or other handling of the dish 930. Advantageously, this movement of the media drop can be reduced by the sloping of the inner lateral surface 944 toward to micro-wells 910, which positions the inner lateral surface 944 closer to the micro-wells 910. This reduces the area in which a media drop stored in the ring 932 can move, and provides a larger contact surface area between the inner lateral surface 944 and the media drop to enhance stability of the media drop. As a result, fluid flow resulting from motion of the media drop can be reduced, which can reduce the likelihood of embryos or pluripotent cells being pulled out of the micro-wells 910 due to motion of the media drop.

Figure 9E:
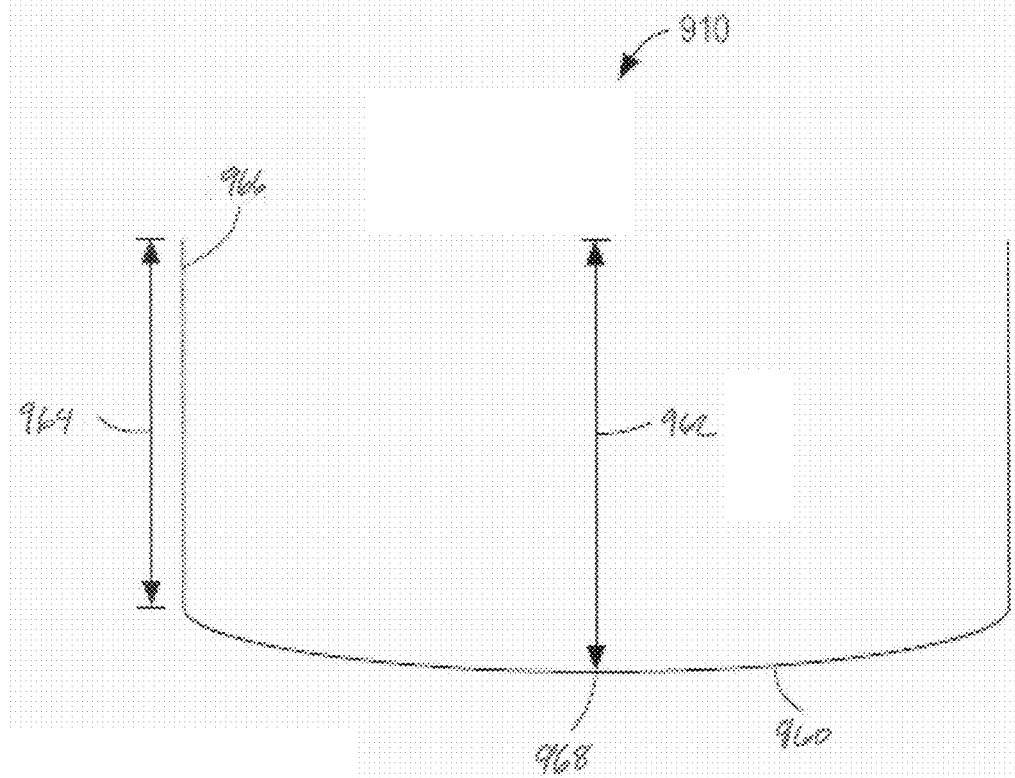

FIG. 9E illustrates a cross-section view of the micro-well 910, according to an embodiment of the invention. In one embodiment, a lower surface 960 of the micro-well 910 may be curved. For example, a first depth 962 at a center 968 of the micro-well 910 may be in the range from about 1.1 to about 1.5 times as large as a second depth 964 at a lateral periphery 966 of the micro-well 910, such as about 1.2 times, about 1.3 times, or about 1.4 times. Alternatively, the lower surface 960 of the micro-well 910 may be substantially planar, such that the first depth 962 is substantially equal to the second depth 964.

Figure 9F:
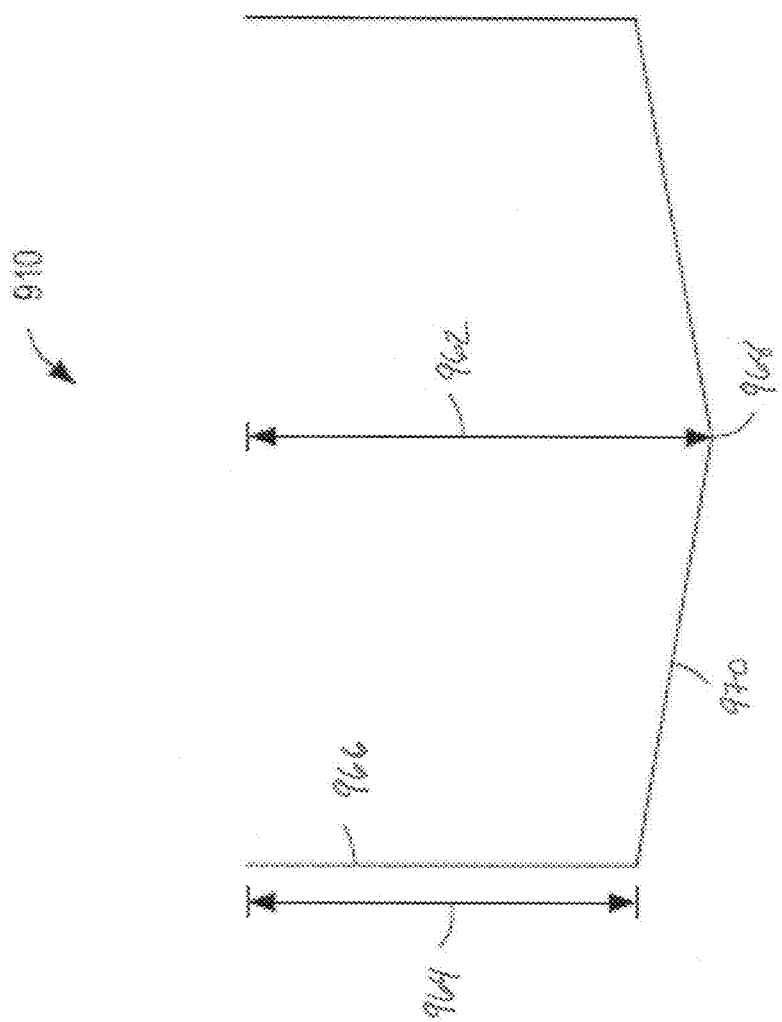

FIG. 9F illustrates a cross-section view of a micro-well 910, according to an embodiment of the invention. The micro-well 910 is in many respects similar to the micro-well 910 described with reference to FIGS. 9A, 9B, and 9E, so differences are described here. A lower surface 970 of the micro-well 910 may be conical. For example, the lower surface 970 may slope downwardly, and substantially linearly, from the lateral periphery 966 to the center 968 of the micro-well 910. As described with reference to FIG. 9E, the first depth 962 may be in the range from about 1.1 to about 1.5 times as large as the second depth 964, such as about 1.2 times, about 1.3 times, or about 1.4 times.

Figure 10:
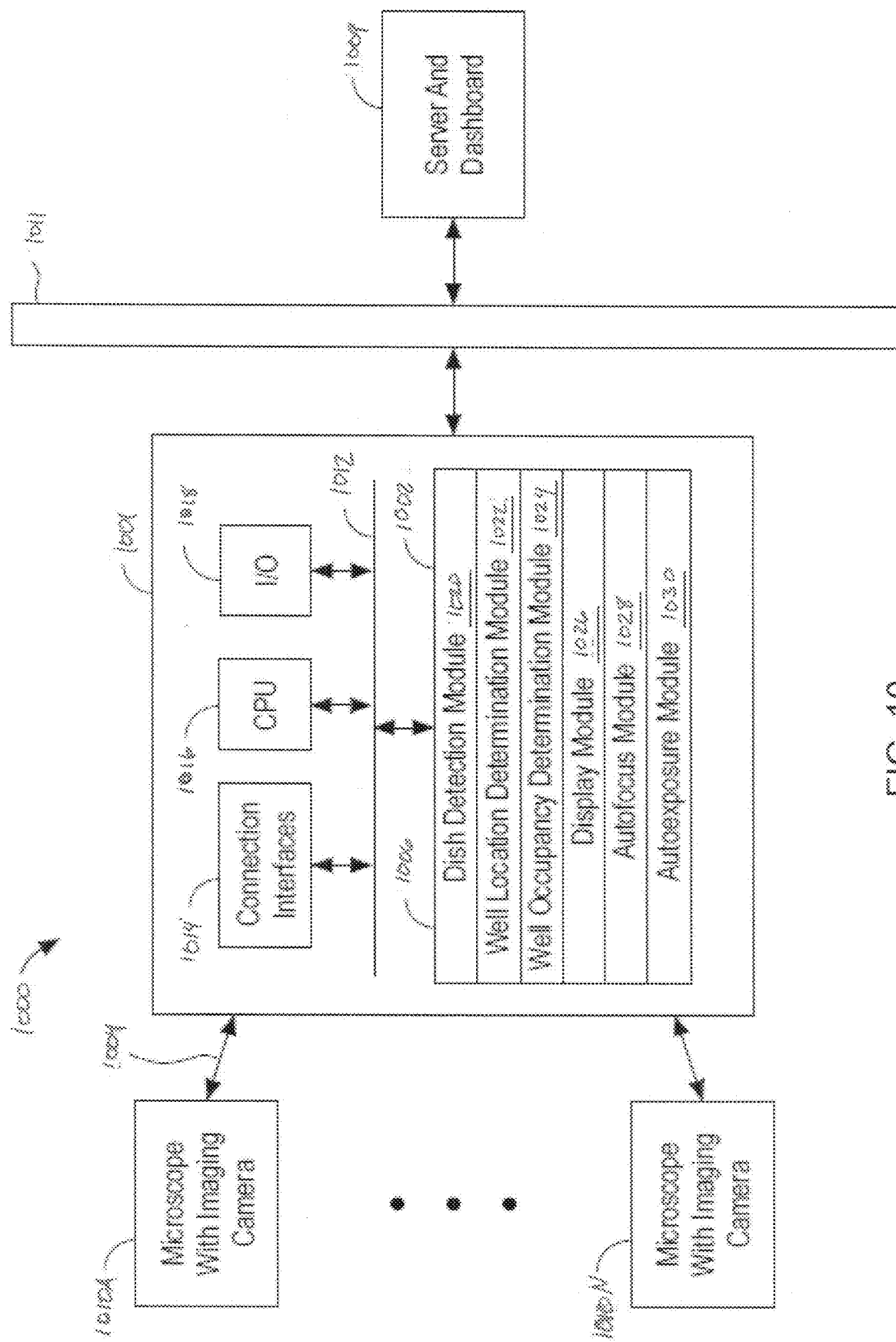
FIG. 10 illustrates a system for automated imaging of human embryos, oocytes, or pluripotent cells including an apparatus for automated dish detection and well occupancy determination, according to an embodiment of the invention.

FIG. 10 illustrates a system 1000 for automated imaging of human embryos, oocytes, or pluripotent cells including an apparatus 1002 for automated dish detection and well occupancy determination, according to an embodiment of the invention. The automated detection of the multi-well culture dish and the determination of well occupancy are processing performed prior to the automated imaging of human embryos. For the subsequent description with reference to FIGS. 10 to 25, the multi-well culture dish is referred to as the multi-well culture dish 900 as described with reference to FIG. 9A, though it is contemplated that the multi-well culture dish can also correspond to the multi-well culture dish 930 as described with reference to FIG. 9C, or to any similar multi-well dish where detection of the dish and determination of occupancy of wells included in the dish can be performed in a similar manner.

The system 1000 includes a microscope controller 1001, which may communicate via a transmission channel 1004 with a set of microscopes with imaging cameras 1010A-1010N. The microscope controller 1001 may be connected to each microscope with imaging camera 1010 via a point-to-point connection, or may be connected to multiple microscopes with imaging cameras 1010 via a network. In one embodiment, the microscope controller 1001 includes standard components, such as connection interfaces 1014, a CPU 1016, and an input/output module 1018, which communicate over a bus 1012. In one embodiment, a memory 1006 connected to the bus 1012 stores a set of executable programs that are used to implement the apparatus 1002 for automated detection of a multi-well culture dish and determination of occupancy of a plurality of micro-wells included in the multi-well culture dish. Alternatively, a processing device (such as circuitry, not shown) connected to the bus 1012 can be used to implement the apparatus 1002 for automated detection of a multi-well culture dish and determination of occupancy of a plurality of micro-wells included in the multi-well culture dish. The microscope controller 1001 may be connected to a server 1009 via a transmission channel 1011, which may be a point-to-point connection or a network. The server 1009 may include a dashboard for providing status information and parameters determined based on analysis of images of a human embryo or pluripotent cell generated by the microscopes with imaging camera 1010.

In an embodiment of the invention, the memory 1006 stores executable instructions establishing a dish detection module 1020, a well location determination module 1022, a well occupancy determination module 1024, and a display module 1026. Alternatively, the processing device (not shown) includes the dish detection module 1020, the well location determination module 1022, the well occupancy determination module 1024, and the display module 1026.

Figure 11:
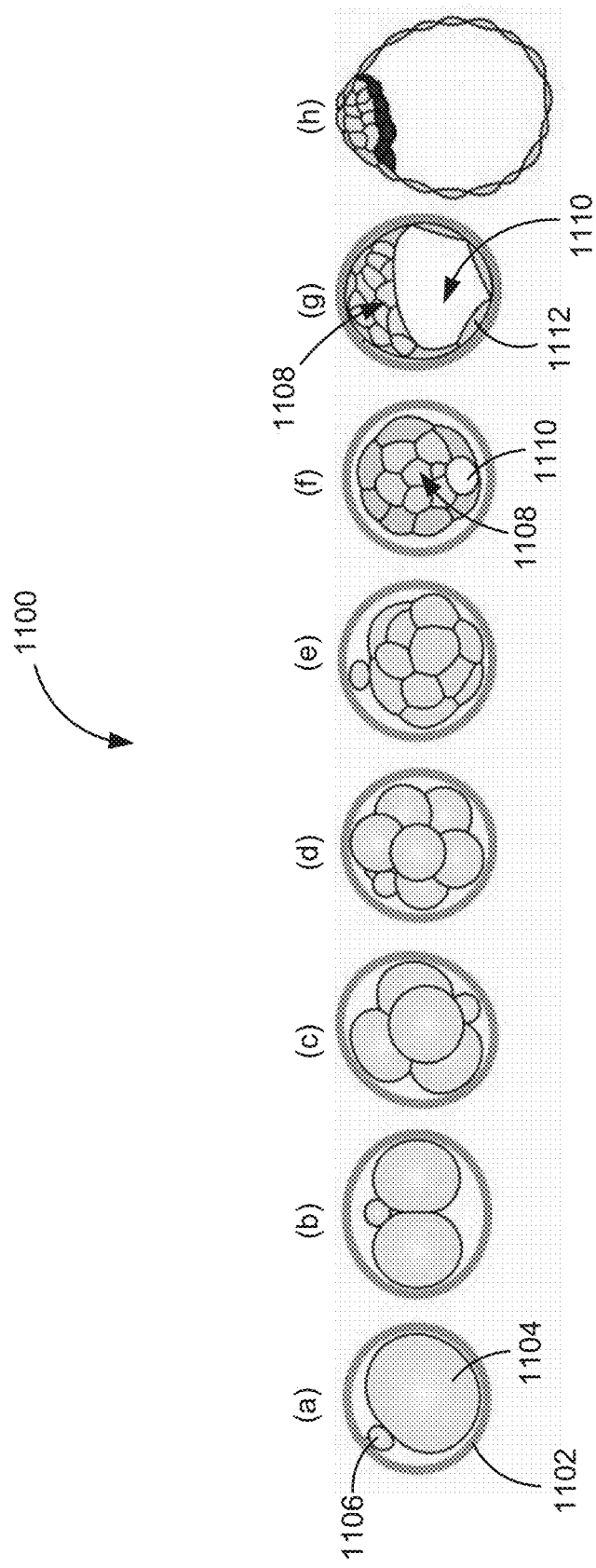
FIG. 11 is a series of images depicting the development of an embryo.

FIG. 11 is a series 1100 of images depicting the development of an embryo, and specifically of a human embryo. The series 1100 of images includes eight images labeled (a), (b), (c), (d), (e), (f), (g), and (h), from left to right respectively. Image (a) identifies an embryo at the time of fertilization. The embryo includes the zona pellucida 1102, a cell 1104, also referred to herein as a blastomere, and the polar body 1106. Image (b) identifies an embryo at the time of the first cleavage event, image (c) identifies the embryo after the second cleavage event, and image (d) identifies the embryo after the third cleavage event and before compaction, whereas image (e) identifies the embryo after the third cleavage event and after compaction. Images (d) and (e) can represent an embryo at approximately 3 days of development.

As seen in image (f), the embryo begins cavitation and an inner cell mass 1108, a trophectoderm 1112, and a cavity 1110 are formed. The embryo and the cavity 1110 grow as depicted in image (g), which image depicts an embryo at approximately day 5 of development. At approximately day 6 of development, the embryo hatches out of the zona pellucida 1102 as indicated in image (h).

Figure 12:
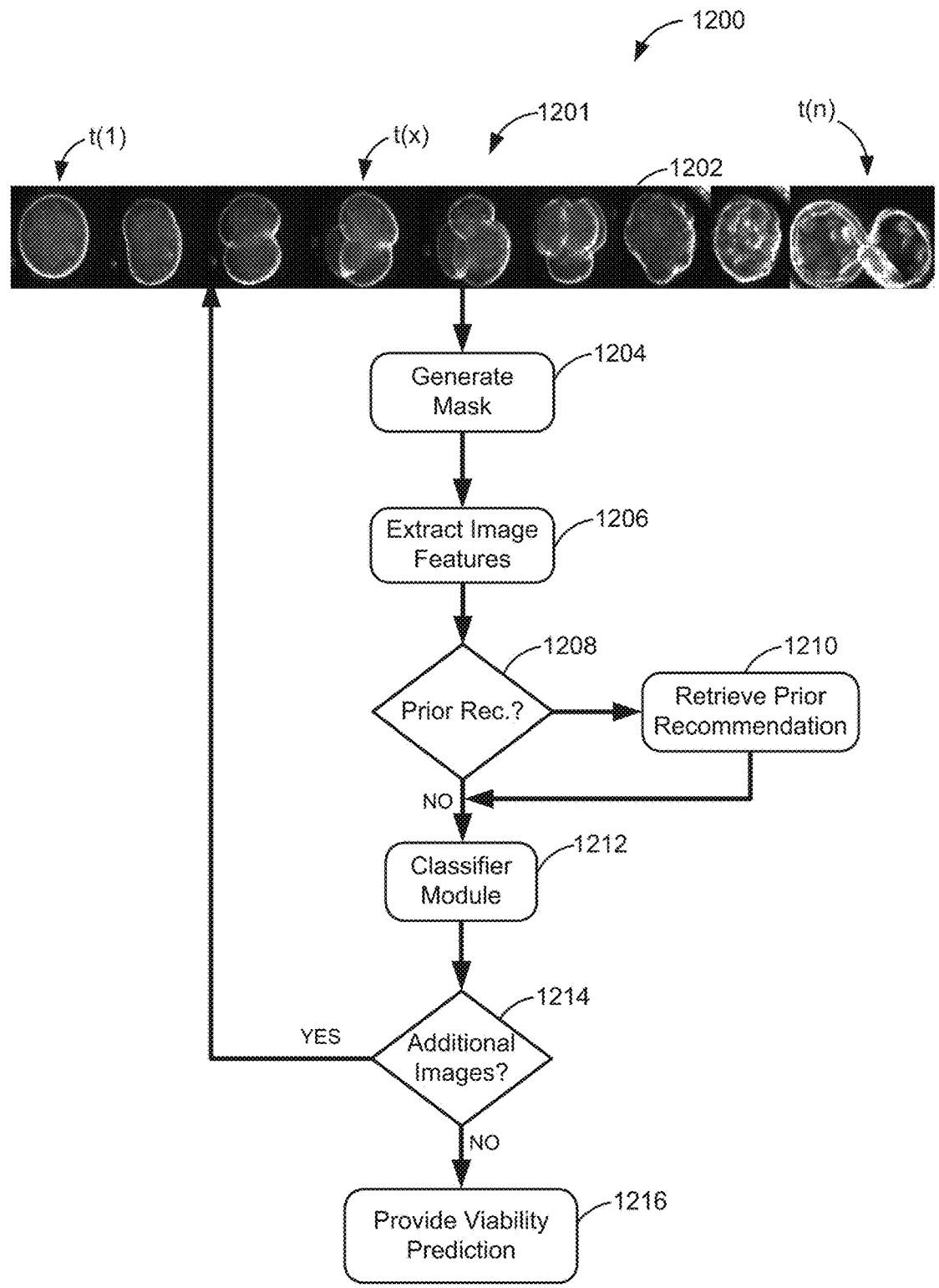
FIG. 12 is a flowchart illustrating one embodiment of a process for predicting viability of an embryo.

FIG. 12 is a flowchart illustrating one embodiment of a process 1200 for predicting viability of an embryo. This viability prediction can include, for example, a prediction of a ploidy status of the embryo such as euploidy or aneuploidy, the prediction of the likelihood of the embryo implanting, or the like. In some embodiments, this viability prediction can include a recommendation for selection of the embryo, a recommendation for de-selection of the embryo, or a non-recommendation of the embryo. In some embodiments, a recommendation for selection can include a recommendation to use one or several embryos, which use can include the implantation of one or several embryos, and in some embodiments a recommendation for de-selection can include a recommendation to not use or to dispose of one or several embryos.

In some embodiments, this viability prediction can be provided to the user via, for example, the dashboard that can be accessible to the user via the input/output module 1018. In some embodiments, the viability prediction can be presented in the form of a ranking of one or several embryos, for example from most likely to be viable and/or most likely to be euploid to least likely to be viable and/or least likely to be euploid. In some embodiments, the viability prediction can include sorting some or all of the embryos amongst one or several categories, which one or several categories can each be, for example, associated with a likelihood of viability and/or a likelihood of euploidy. In one embodiment, for example, the embryos can be sorted amongst two, three, four, five, or six categories with the first category associated with the greatest likelihood of viability and/or euploidy, with the fifth category associated with the smallest likelihood of viability and/or euploidy, and the remaining categories having likelihoods of viability and/or euploidy intermediate between the first and fifth categories.

The process 1200 begins at 1202 wherein a series of images, and specifically wherein a series of time lapse images 1201 is received. In some embodiments, this series of images 1201 can be of a culture dish, such as multi-well culture dish 215. In some embodiments, the culture dish can be located on the stage of the microscope. In some embodiments, this series of images 1201 can include one or several embryos such as human embryo located in, for example, one or several of the plurality of wells of the multi-well culture dish 215 can be received from one or several of the microscopes with imaging cameras 1010 depicted in FIG. 10. In some embodiments, this series of images 1201 may be generated and/or captured by one or several cameras of the one or several of the microscopes with imaging cameras 1010.

Referring to the series of time-lapse images 1201, the series 1201 can include any desired number of images that can, for example have a constant time interval between images or a varied time interval between images. These images can comprise image data that can, for example, include data identifying an attribute of some or all of the pixels forming each of the images including, for example, a pixel color, brightness, intensity, contrast, or the like.

In some embodiments, this series 1201 can extend from a first image t(1) to a final image t(n). In some embodiments, the first image t(1) can be the first image captured by the camera, and in some embodiments, the first image t(1) can be designated based on its position relative to an anchor.

This anchor can be, for example, a common and/or universal embryonic event such as, for example, one of the first, second, and third cleavage events, cavitation, hatching, or the like. In some embodiments, this position relative to the anchor can be a number of image frames before or after the anchor, an amount of time before or after the anchor, or the like. In one embodiment, for example, the anchor can be the first cleavage event, and the position relative to the anchor can be, for example, at a frame between 0 and 5,000 frames before or after the anchor event, at a frame between 0 and 1,000 frames before or after the anchor event, at a frame between 0 and 500 frames before of the anchor event, at a frame between 0 and 200 frames before or after the anchor event, at a frame between 0 and 100 frames before or after the anchor event, at a frame between 25 and 75 frames before or after the anchor event, or any other or intermediate position relative to the anchor. In some embodiment, the anchor can enable the use of a wavelet transform.

After the series of images has been received, the process 1200 proceeds to block 1204 wherein a mask is generated. In some embodiments, the mask can be placed over portions of one or several of the series of images to block those portions of the one or several of the series of images to facilitate viewing and/or analysis of the unmasked portions of the one or several of the series of images. Thus, in some embodiments, the mask, also referred to herein as an embryo mask, distinguishes between a first portion of the image and a second portion of the image. In some embodiments, the first portion contains the image of the embryo, and the second portion does not contain the image of the embryo.

In some embodiments a mask can be generated for each of the images in the series of images and can thus be unique for the image for which it is generated, and in some embodiments, a mask can be generated for a plurality of the images in the series of images. As used herein, "background" refers to portions of one or several images blocked/obscured by the mask, and is used herein, "foreground" refused to portions of one or several images that are not blocked/not obscured by the mask.

Figure 13:
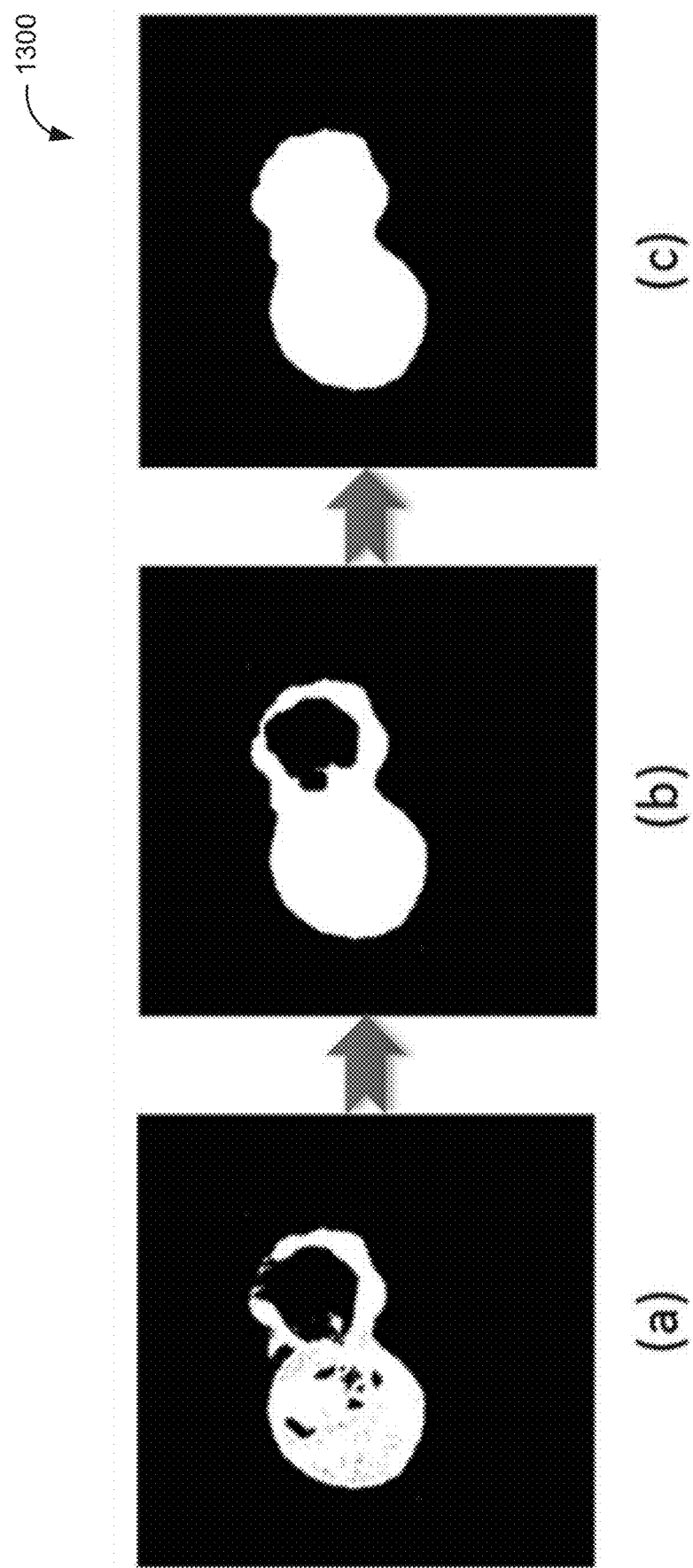
FIG. 13 is a schematic illustration of an exemplary process for the creation of the mask is shown.

One embodiment of an exemplary process 1300 for the creation of the mask is shown in FIG. 13. This process 1300 is depicted by a series of images of a mask created for a hatching embryo. These images progress from left to right, starting with image (a) and ending with image (c). In these images, the zona pellucida and the area enclosed by the zona pellucida forms the left-most, white, spherical portion and the blastocycst as defined by the trophectoderm forms the right-most, white portions of the image. In images (a) and (b), the cavity within the blastocyst is visible as the black enclosed area within the right-most, white portion of the image. This cavity portion is filled, and thus appears white in image (c). The use of masks as shown in FIG. 13 can enable evaluation of image aspects, and extraction of one or several image features relating to the cavity such as the area of the cavity, the perimeter of the cavity, the area of the embryo including or excluding the cavity area, or the like. Further, the use of masks as shown in FIG. 13 can enable evaluation of image aspects and extraction of one or several image features relating to the hatching, the zona pellucida, the trophectoderm, the inner cell mass, and/or other embryonic structures.

This process 1300 begins with the evaluation of portions of one or several images of the series of images for mask classification. In some embodiments, these portions can be, for example, one or several pixels, one or several groups of pixels, or the like. This mask classification can include, for example, determining whether the evaluated portions are part of the background or are part of the foreground. In some embodiments, evaluated portions are identified as part of the background if they are outside of the image of the embryo and thus not part of the image of the embryo, and evaluated portions are identified as part of the foreground if they are inside of the embryo and thus part of the embryo. This evaluation can be performed by a mask classifier which can be, for example, a software module located within the server 1009 or within the microscope controller 1001.

After the evaluation of portions of one or several images of the series of images for mask classification, the mask classifier can generate and output a preliminary mask, also referred to herein as a preliminary mask image. In some embodiments, the mask classifier can generate and output a preliminary mask based on the results of the evaluation of portions of one or several images of the series of images for mask classification, and specifically based on results of the evaluation of portions of one or several of the images of the series of images as inside of the mask area or outsides of the mask area. An exemplary embodiment of a preliminary mask is depicted in image (a) of FIG. 13. As seen in image (a), the preliminary mask can include one or several holes (see as black portions within the left-most, white, circular portion of the image (a).

After the preliminary mask is been generated, the process 1300 proceeds to refine the preliminary mask. In some embodiments, the refinement can include identifying one or several continuous, foreground components. These components can be identified via Connected Component Analysis, and in some embodiments, all but one or several designated identified components can be removed from the foreground, and particularly, all but the largest one or several of these components can be removed from the foreground. In some embodiments, Connected Component Analysis can be performed using any commercially or open source available Connected Component Analysis software or code.

The refinement can further include the identification and filing of one or several holes enclosed, or partially enclosed within the foreground portions of the mask. This can be performed via hole filing, dilation, or other post processing technique. In some embodiments, the hole filing and/or dilation can be performed using available hole filing and/or dilation software or code.

Through the Connected Component Analysis and the hole filing, the mask can be refined such that the foreground and background portions of the mask are more continuous as depicted in images (b) and (c). In some embodiments, this refinement can be an iterative process involving repeated steps. In the images of FIG. 13, image (b) has been iteratively less-refined than image (c). Thus, as seen in image (b), the cavity is still unfilled in the right-most, white portion of the image. Accordingly, the cavity of the embryo is in the background. As further seen in image (b), the white image portions surrounding the cavity are more continuous than in image (a) and the holes have been removed from left-most, white portion of the image (b).

In some embodiments, a first mask consistent with image (c) can be created. Further, in some embodiments, a series of first masks can be created for some or all of the images in the series of images, and particularly, a unique first mask can be created for each of the images in the series of images from the image in the series of images for which that unique first mask was created. These first masks can be stored in, for example, the memory 1006.

This first mask can place a first area in the background. Thus, this first mask can obscure the first area when overlaying one image of the series of images 1201. In some embodiments, this second area can include some or all of the areas outside of the embryo, including outside of the zona pellucida.

In some embodiments, an area of the first mask can be determined. As used herein, the area of the first mask can refer to the area of the foreground portion unobscured by the first mask when the first mask is overlaid on one of the images in the series of images, and particularly when the first mask is overlaid on the image in the series of images from which the first mask was created. In some embodiments, this first area of the mask can be determined by determining the number of pixels in the foreground when the first mask is overlaid on the image in the series of images. This first mask area can be determined for some or all of the images in the series of images using the first mask created for each of the some or all of the images in the series of images. These first mask areas can be stored in the memory 1006.

In some embodiments, a second mask consistent with the image (b) can be created. Further, in some embodiments, a series of second masks can be created for some or all of the images in the series of images, and particularly, a unique second mask can be created for each of the images in the series of images from the image in the series of images for which that unique second mask was created. These second masks can be stored in, for example, the memory 1006.

This second mask places a second area in the background. Thus, the second mask obscures the second area when overlaying one image of the series of images 1201. This second area can include the first area, as well as one or several internal portions of the embryo, and specifically one or several portions of the cavity. Thus, as seen in image (b), the area outside of the embryo including outside of the zona pellucida, and the area of the cavity are in the background. A mask that has gone through refinement is referred to herein as one of the first mask or the second mask, or as a refined mask or a final mask.

In some embodiments, an area of the second mask can be determined. As used herein, the area of the second mask can refer to the area of the foreground portion unobscured by the second mask when the second mask is overlaid on one of the images in the series of images, and particularly when the second mask is overlaid on the image in the series of images from which the second mask was created. In some embodiments, this second area of the mask can be determined by determining the number of pixels in the foreground when the second mask is overlaid on the image in the series of images. This second mask area can be determined for some or all of the images in the series of images using the second mask created for each of the some or all of the images in the series of images. These second mask areas can be stored in the memory 1006. Further, in some embodiments, one or several calculations can be performed using the first and second mask areas. In some embodiments, this can include determining differences for one or several of the first and second masks area.

Returning again to FIG. 12, after the mask has been generated and applied, superimposed, and/or overlaid on the image, with which it is associated, the process 1200 proceeds to block 1206, wherein one or several image features, also referred to herein as image-based features, are extracted from one or several of the images of the series of images. In some embodiments, the applying, superimposing, or overlaying of the mask on the image with which the mask is associated can enable identification of at least one of: cavitation; and hatching. Specifically, in some embodiments, the use of the masks described herein enable detection of a feature of one or several of the images based on the embryo mask.

In some embodiments, these one or several features can be automatically extracted, and in some embodiments, these one or several features can be only automatically extracted such that they are not manually measured and/or determined. Thus, in such embodiments, these one or several image features can be extracted from the series of images by, for example, the server 1009 or the microscope controller 1001 without any substantive human inputs or any substantive human action. These one or several image features can be stored in, for example, the memory 1006.

The image features can be any features that can be extracted from one or several of the images of the series of images. In some embodiments these images features relate to one or several of the images of the series of images, and in some embodiments, these image features relate to all of the images of the series of images. These image features can, for example, relate to one or more of: cavitation; hatching; embryo expansion; and embryo collapse, and in some embodiments, these image features can relate to at least one of: an area of the embryo; an area of a cavity of the embryo; a perimeter of the embryo; and a convex hull of the embryo. In some embodiments, image features relating to cavitation, also referred to herein as cavitation features, can relate to at least one of: embryo image area; cavity image area; a change in embryo image area over time; a change in cavity image area over time; embryo image perimeter; and convex hull. In some embodiments, the cavitation features can relate to: an average cepstrum of an embryo attribute; a final embryo area; a maximum embryo area; an average embryo area; a number of cavitation peaks; a final cavitation area; a maximum cavitation area; a maximum embryo area difference; a maximum cavitation area difference; a mean ration of cavitation and embryo areas; a mean area of cavitation; and a maximum ratio of cavitation and embryo areas.

The image features can be extracted in a variety of different ways that depend on the details of the specific image feature being extracted. In some embodiments, for example, the image features can be extracted based on one or several properties of one or both of the first and second masks. Thus, in some embodiments, one or image features can be determined based on: the area and/or perimeter of one or both of the masks; the difference in areas of the first and second masks; and the shape of all or portions of one or both of the first and second masks.

In some embodiments, the extraction of the image features can further include the application of one or several transforms or analysis techniques to data extracted from all or portions of the series of images. These transforms or analysis techniques can include, for example, at least one of: a Fourier transform, including a Discrete Fourier Transform (DFT); a cepstrum transform that can be calculated as the inverse DFT of the log magnitude of the DFT of the extracted data; and a wavelet transform such as a discrete wavelet transform. In some embodiments, the discrete wavelet transform comprises one of: Haar wavelet; Daubechies wavelets; Symlets wavelets; Battle-Lemarie wavelets; and Biorthogonal wavelets.

To calculate a cepstrum, a time-series of extracted data is created across some or all of the images of the series of images. In some embodiments, this extracted data can be an untransformed image feature and the time series of extracted data can be a 1D vector of floating-point numbers. The following computation can be applied to this 1D vector:

$$|\mathscr{F}^{-1}\{\log(|\mathscr{F}\{f(t)\}|^2)\}|^2$$

In this expression, $\mathscr{F}$ represents the Fourier Transform and $\mathscr{F}^{-1}$ represents the Inverse Fourier Transform. After applying discretization on the continuous variable t f(t)→$f_t$ (where t∈Z and Z indicates the set of integer values), these transforms become (for N time-samples):

$$\hat{f}_\omega = \mathscr{F}\{f_t\} = \sum_{t=0}^{N-1} f_t e^{-2\pi i wt/N}, \omega \in Z$$

and:

$$f_t = \mathscr{F}^{-1}\{\hat{f}_\omega\} = \sum_{\omega=0}^{N-1} \hat{f}_\omega e^{+2\pi i wt/N}, t \in Z$$

The output of these expressions is a transformed 1D vector corresponding to the 1D vector to which the transform was applied. In some embodiments, the mean value of that transformed 1D vector can be calculated, which mean value is referred to herein as a "mean cepstrum."

Exemplary image features are listed in Table 1, below. Any one of the image features listed in Table 1 may be used alone or in combination with each other or other features.

TABLE 1

List of Image Features

Figure 14:
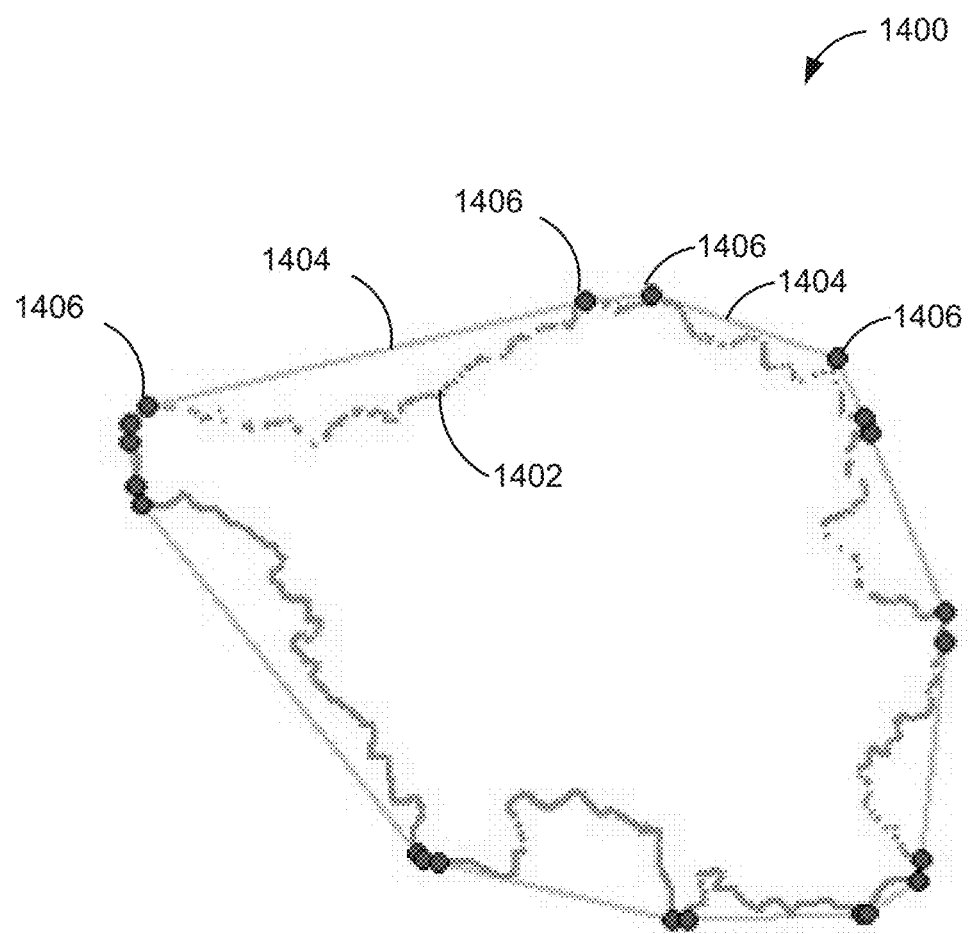
FIG. 14 is a schematic illustration of one embodiment of a generated convex hull.

| Image Feature | Description/Reference describing Image Feature |
|---|---|
| Mean Cepstrum of the Embryo Area | This is the average cepstrum of the embryo area for some or all of the images of the series of images. The area of the embryo including the cavity is determined by the area of the first mask. The mean cepstrum of the embryo area is calculated by: determining the area of the embryo in some or all of the images of the series of images; calculating the cepstrum for each of the determined areas of the embryo; and calculating the average cepstrum. |
| Mean Cepstrum of the Embryo Perimeter | This is the average cepstrum of embryo perimeter for some or all of the images of the series of images. The perimeter of the embryo is the geodesic distance around the mask. The mean cepstrum of the embryo perimeter is calculated by: determining the perimeter of the embryo in some or all of the images of the series of images; calculating the cepstrum for each of the determined perimeters of the embryo; and calculating the average cepstrum. |
| Mean Cepstrum of the Number of Convex Hull Points | This is the average cepstrum of the number of convex hull points for some or all of the images of the series of images. The number of convex hull points is the minimum number of points located on the perimeter of the mask or on the perimeter of the image of the embryo that define lines that together circumscribe the mask or the image of the embryo.<br>FIG. 14 depicts a convex hull 1400 generated so as to circumscribe an image of embryo 1402. As seen in FIG. 14, the convex hull 1400 is generated by a plurality of line segments 1404 extending between points 1406 which are located on the perimeter of the embryo 1400 and/or mask. In some embodiments, the points 1406 can be positioned on the perimeter of the image of the embryo 1402 and/or mask such that the minimum number of points 1406 is generated to define the smallest number of line segments 1404 to circumscribe and enclose the embryo 1402 and/or mask without the line segments crossing into or over the image of the embryo 1402 and/or mask. The mean cepstrum of the number of convex hull points is calculated by: determining the number of convex hull points in some or all of the images of the series of images; calculating the cepstrum for each of the determined numbers of convex hull points; and calculating the average cepstrum. |
| Final Embryo Area | This is the area of the embryo including the cavity at the final image in the series of images. This final area is the area of the first mask for that final image. |
| Max Embryo Area | This is the maximum area of the embryo, including the cavity, in any image of the series of images. This maximum area can be calculated by determining the area of the first mask for each of some or all of the images of the series of images, and identifying the maximum value of those determined areas. |
| Mean Embryo Area | This is the average area of the embryo including the cavity calculated for some or all of the images of the series of images. This average embryo area is calculated by determining the area of the first mask for each of the some or all of the images of the series of images, and calculating the average of those determined areas. |
| Number of Cavitation Peaks | This is the number of maxima of cavitation volume in the series of images. This is calculated by determining the cavitation area in some or all of the images in the series of images, identifying images with a larger cavitation area than their adjacent images, and incrementing a count for each such identified image. |
| Final Cavitation Area | This is the area of the cavity at the final image in the series of images. This final area is the area of the first mask for that final image minus the second mask for that final image. |
| Max Cavitation Area | This is the maximum area of the cavity, in any image of the series of images. This maximum area can be calculated by determining the area of the cavity by subtracting the area of the second mask from the area of the first mask for each of some or all of the images of the series of images, and identifying the maximum value of those determined areas. |
| Max Embryo Area Difference | This is the maximum absolute difference in embryo area between adjacent images in the series of images. This is calculated by: determining the area of the first mask in some or all of the images of the series of images; identifying one or several pairs of adjacent images in the series of images; taking the absolute |

TABLE 1-continued

List of Image Features

| Image Feature | Description/Reference describing Image Feature |
|---|---|
| | value of the differences between the areas of the images of the identified pairs of adjacent images; and identifying the largest of the absolute values of these differences. |
| Max Cavitation Area Difference | This is the maximum difference in cavitation area between adjacent images in the series of images. This is calculated by: determining the difference between the first and second masks (cavitation area) for some or all of the images in the series of images; identifying one or several pair of adjacent images in the series of images; and identifying the largest of the differences between the cavitation area of the adjacent images in the pairs. |
| Mean Ratio of Cavitation and Embryo Areas | This is mean ratio of cavitation and embryo areas for some or all of the images in the series of images. This is calculated by calculating the ratio of cavitation and embryo areas for some or all of the images in the series of images by dividing the cavitation area (area of the first mask minus the area of the second mask) by the embryo area (area of the first mask). The average value of these ratios is then calculated. |
| Mean Cavitation Area | This is the average cavitation area for some or all of the images in the series of images. This is calculated by identifying the cavitation area for some or all of the images in the series of images (area of the first mask minus the area of the second mask); and calculating the average value of these cavitation areas. |
| Maximum Ratio of Cavitation and Embryo | This is the maximum value of the ratio of cavitation and embryo areas for some or all of the images in the series of images. This is calculated by calculating the ratio of cavitation and embryo areas for some or all of the images in the series of images by dividing the cavitation area (area of the first mask minus the area of the second mask) by the embryo area (area of the first mask); and identifying the largest calculated ratio. |
| $2^{nd}$ Max Embryo Area | This is the second largest area of the embryo, including the cavity, in any image of the series of images. This second largest area can be calculated by determining the area of the first mask for each of some or all of the images of the series of images, and identifying the second largest value of those determined areas. |
| $3^{rd}$ Max Embryo Area | This is the third largest area of the embryo, including the cavity, in any image of the series of images. This third largest area can be calculated by determining the area of the first mask for each of some or all of the images of the series of images, and identifying the third largest value of those determined areas. |
| $2^{nd}$ Max Cavitation Area | This is the second largest area of the cavity, in any image of the series of images. This second largest area can be calculated by determining the area of the cavity by subtracting the area of the second mask from the area of the first mask for each of some or all of the images of the series of images, and identifying the second largest value of those determined areas. |
| $3^{rd}$ Max Cavitation Area | This is the third largest area of the cavity, in any image of the series of images. This third largest area can be calculated by determining the area of the cavity by subtracting the area of the second mask from the area of the first mask for each of some or all of the images of the series of images, and identifying the third largest value of those determined areas. |
| Mean Cepstrum of Std. Dev. Of Hessian Features | This is the average cepstrum value of the standard deviation of Hessian features for some or all of the images in the series of images, which Hessian features can be a, for example, the coarsest resolution. In some embodiments, the Hessian is the result of: 1) coarse-grain smoothing such as occurs, for example, when using a Gaussian filter with standard deviation of, for example, 5 pixels; and (2) applying a 2nd order derivative filtering in X and Y at some or all of the pixels in a selected image. These yield a Hessian matrix for the pixels to which this was applies. In some embodiments, the smallest eigenvalue can be extracted from this matrix, and the standard deviation of these smallest, extracted eigenvalues can be calculated for each image across some or all of the pixels in that image. The cepstrum transform is applied to the standard deviation of the smallest eigenvalues, and the average value of the result of this transform is calculated. |
| Mean Cepstrum of Std. Dev. Of Continuity | This is the average cepstrum value of the standard deviation of continuity for some or all of the images in the series of images. The continuity is obtained from the embryo boundary by: expressing the boundary in polar coordinates using the embryo region's center of mass as the origin; and calculating the absolute value of changes in the radius as a function of change in angle for fixed angular increments.<br>This calculated value is mathematically expressed as $\left\|\frac{\Delta r}{\Delta \theta}\right\|$.<br>The absolute value of the difference between each calculated value $\left(\left\|\frac{\Delta r}{\Delta \theta}\right\|\right)$ and the average of all of those calculated values $\left(\left\|\frac{\Delta r}{\Delta \theta}\right\|\right)$ is calculated, and the standard deviation of those absolute values is calculated resulting in the creation of a time series of standard deviations. The cepstrum transform is applied to this time series of standard deviations, and the output of the cepstrum transform is averaged. |

TABLE 1-continued

List of Image Features

| Image Feature | Description/Reference describing Image Feature |
|---|---|
| Mean Cepstrum of Mean Continuity | This is the average cepstrum value of the mean continuity for some or all of the images in the series of images. The continuity is obtained from the embryo boundary by: expressing the boundary in polar coordinates using the embryo region's center of mass as the origin; and calculating the absolute value of changes in the radius as a function of change in angle for fixed angular increments. This calculated value is mathematically expressed as $\left\|\frac{\Delta r}{\Delta \theta}\right\|$. The absolute value of the difference between each calculated value $\left(\left\|\frac{\Delta r}{\Delta \theta}\right\|\right)$ and the average of all of those calculated values $\left(\overline{\left\|\frac{\Delta r}{\Delta \theta}\right\|}\right)$ is calculated, and the mean of those absolute values is calculated resulting in the creation of a first time series of means. The cepstrum transform is applied to this time series of means and the output of the cepstrum transform is then averaged. |

Although the above identifies the first, second, and third maximum values for embryo area and cavitation area, additional maximum values for embryo area and cavitation area can be used. These can include, for example, the $4^{th}$ largest, $5^{th}$ largest, $6^{th}$ largest, $7^{th}$ largest, $8^{th}$ largest, $9^{th}$ largest, $10^{th}$ largest, and/or any other maximum values.

In some embodiments, these one or several image features were identified and/or selected based on their effectiveness in contributing to the generation of a viability prediction. For this selection, a set of data was received randomly partitioned into a training set and a testing set. In some embodiments, this partition was done following a fixed proportion, also known as a split-ratio. After the partitioning of the data, a statistical model was trained with the training-set and the effectiveness of the model was determined with the testing set. These steps were iterated until a desired number of iterations had occurred, and then the average predictive power of the model is calculated.

In some embodiments, the predictive power of the statistical model, and the effectiveness of image features or other features used in that statistical model can be determined through the calculation of a Fisher score, which is a measure of inter-class scatter divided by intra-class scatter. The Fisher score is given by:

$$S = \frac{\sigma_{between}^2}{\sigma_{within}^2} = \frac{(w^T \mu_{+1} - w^T \mu_{-1})^2}{w^T \Sigma_{+1} w + w^T \Sigma_{-1} w} = \frac{(w^T (\mu_{+1} - \mu_{-1}))^2}{w^T (\Sigma_{+1} + \Sigma_{-1}) w}$$

and $$w \propto (\Sigma_{+1} + \Sigma^{-1})^{-1} (\mu_{+1} - \mu_{-1})$$

In the expressions above, the subscripts indicate 2 labels indicative of desired predicted states or classifications. In this specific instance, the classifications are viable/nonviable, which can also include euploid/non-euploid, euploid/aneuploid, aneuploidy/non-aneuploidy, implant/non-implant, or the like. As specifically identified, "+1" in the above expressions identifies euploid and "−1" identifies aneuploidy. In the above expressions, $\mu_{+1}$ indicates the mean value of feature-vectors which are labeled as +1 (a vector), $\mu_{-1}$ indicates the mean value of feature-vectors which are labeled as 11 (a vector), $\Sigma_{+1}$ indicates the covariance (a matrix, defined as the mean-centered $2^{nd}$ moment) of the feature-vectors which are labeled as +1, and $\Sigma_{-1}$ indicates the covariance (a matrix, defined as the mean-centered $2^{nd}$ moment) of the feature-vectors which are labeled as −1.

After Fisher scores are calculated, the effectiveness of the model and/or of one or several of the image features or other parameters can be ascertained with the Fisher score. In some embodiments, for example, a larger Fisher score can be indicative of a more effective model and/or feature, and thus features can be selected that have the highest Fisher scores and/or a model can be accepted when it has the highest Fisher score of a group of models, or when its Fisher score reaches a predetermined threshold level.

In some embodiments the image features extracted from all or portions of the series of images can be supplemented by one or several other parameters. These one or several other parameters can be inputted into the system and can, for example, relate to the age of the human source of the egg at the time of egg harvesting, the age of the egg since harvesting, past medical history of the human source of the egg, information relating to past success or failure with IVF, or the like. In some embodiments, these one or several other parameters can be received from a user via the input/output module 1018 and can be stored in the memory 1006.

In some embodiments, these other parameters can include, for example, one or several prior recommendations or prior viability predictions. In some embodiments, for example, images can be received for evaluation shortly after they have been captured. In such an embodiment, it can be advantageous to generate evaluate viability based on the images already received and not wait for the completion of capturing all of the images in the series of images. In some such embodiments, an initial recommendation can be generated based on the evaluated one or several images, but this recommendation can be updated as further images are received.

In some embodiments, different parameters may be used in generating a recommendation for images of embryos in different developmental stages. In one embodiment, for example, a first recommendation can be generated based on images generated up to the third day of development, as corresponding with images (d) and (e) of FIG. 11. In such embodiments, the first recommendation can be generated based on image features extracted from the received images and/or from one or several other parameters. In one embodiment, for example, the first recommendation can be generated based on: the duration of the first cytokinesis, the length of the time interval between the first cytokinesis and the second cytokinesis, the length of the time interval between the second cytokinesis and the third cytokinesis, the age of the human source of the egg at the time of egg harvesting, a cell count, which can be a manual cell count, at the end of the time period for the first recommendation, and a result of a morphological analysis, which can be manually performed. In some embodiments, the age of the human source of the egg at the time of egg harvesting, a manually performed cell count, and a manually performed morphological analysis are all examples of manual biological measurements.

In some embodiments, the length of the time interval between the first cytokinesis and the second cytokinesis can be, for example, the time from 2-cell embryo to 3-cell embryo, the time from the end of the first cytokinesis to the end of the second cytokinesis, the duration of time as a 2 cell embryo, and/or any other measure of the duration of this time period. In some embodiments, the length of the time interval between the second cytokinesis and the third cytokinesis can be, for example, the time from 3-cell embryo to 4-cell embryo, the time from the end of the second cytokinesis to the end of the third cytokinesis, the duration of time in which the embryo was 3 cell embryo, and/or any other measure of this time period.

After the one or several image features have been extracted, the process 1200 proceeds to decision block 1208, wherein it is determined if there were any prior recommendations. In one embodiment, for example, a prior recommendation can be generated based on images from t(0) to t(x), and a further recommendation can be based on, for example, images from t(0) to t(n), images from t(x) to t(n), and/or any other set of images. If it is determined that there is a prior recommendation, then the process 1200 proceeds to block 1210, wherein the prior recommendation is retrieved from, for example, the memory 1006.

After the prior recommendation has been retrieved, or returning again to decision block 1208, if it is determined that there are no prior recommendations, the process 1200 proceeds to block 1212, wherein the one or several image features are inputted into a machine learning module, also referred to as a classification module, configured for generation of a viability prediction based on the received image features, and specifically based on one or several features such as a cavitation or cavitation related feature, a feature including a cepstrum such as a cavitation cepstrum, or any other image feature identified above. Thus, in some embodiments, the machine learning module can generate a viability predication, with can include a prediction of euploidy or aneuploidy, a prediction of the likelihood of the embryo implanting, or the like.

In some embodiments, and as depicted in FIG. 12, this machine learning module can be one or several classifiers that are usable for outcome determination. Any suitable classifier may be employed. In some embodiments, the classifier is based on a machine learning algorithm. The classifier may be an AdaBoost (adaptive boosting) classifier, a Support Vector Machine (SVM), a Naïve Bayes classifier, a classifier using an ensemble method such as a Random Forest classifier, or a Boosting Tree. In some embodiments, an ensemble method classifier that uses multiple learning algorithms to obtain better predictive performance than could be obtained by using any of that multitude of learning algorithms alone. Thus, this in effect groups several "weak learners" together to form a "strong learner."

In some embodiments, classifiers can be arranged into multiple levels, and in some embodiments, each of these multiple levels can include one or several classifiers. In some embodiments, a refining algorithm can be applied to the output of the last image classifier to further refine the classification of the image. In some embodiments, the refining algorithm refines the classification of each image based on a temporal image similarity measure of the image. In some embodiments, the refining algorithm is a dynamic programming algorithm for finding the most likely classification of the images included in the time-lapse series of images. In some embodiments, the refining algorithm is a Viterbi algorithm.

After the one or several image features are inputted into a machine learning module, the classifier generates a viability prediction. In some embodiments, this viability prediction can be based only on the inputted image features, and in some embodiments, this viability prediction can be based on the inputted image features and one or several other parameters such as, for example, age of the human source of the egg at the time of egg harvesting, a prior recommendation, or the like. In some embodiments, this viability prediction can be based on a cavitation or cavitation related feature, a feature including a cepstrum such as a cavitation cepstrum, or any other image feature identified above.

In some embodiments, this viability prediction can be automatically generated, and specifically can be generated based on the inputted features by, for example, the server 1009 or the microscope controller 1001 without any manual biological measurements, without any substantive human inputs, and/or without any substantive human action. As used herein a "substantive human input" and a "substantive human action" do not include inputs or actions to start or continue all or portions of the process 1200 shown in FIG. 12 and/or relating to non-outcome determinative action or input. In some embodiments, the viability prediction can be stored in the memory 1006.

In some embodiments, the classifier can generate the viability prediction based on training of the classifier. This training can be based on a data set, and particularly on a data set repeatedly, randomly partition into a training set and a testing set. This training can proceed as discussed above until a desired measure of effectiveness of the classifier is achieved. As a result of the training of the classifier, the classifier can generate a viability prediction based on inputs received by the classifier.

After the image features are inputted into the classifier and after the classifier generates a viability prediction, the process 1200 proceeds to decision block 1214, wherein it is determined if additional images have been generated. In some embodiments, this can include determining whether further images have been generated and/or received that were not included in the generation of the viability prediction by the classifier in block 1212. If it is determined that there are additional images, then the process 1200 returns to block 1202, and proceeds as outlined above.

If it is determined that there are no additional images, then the process 1200 proceeds to block 1216, wherein the viability prediction is provided. In some embodiments, the viability prediction can be provided to the user via the input/output module 1018 and specifically via the GUI. In some embodiments, the outputted viability prediction can include the outputting of one or several categories into which one or several imaged embryos have been placed, the outputting of a ranking of one or several embryos relative to each other, which ranking can identify the embryos that are most likely to be viable or least likely to be viable, or the like.

Figure 15:
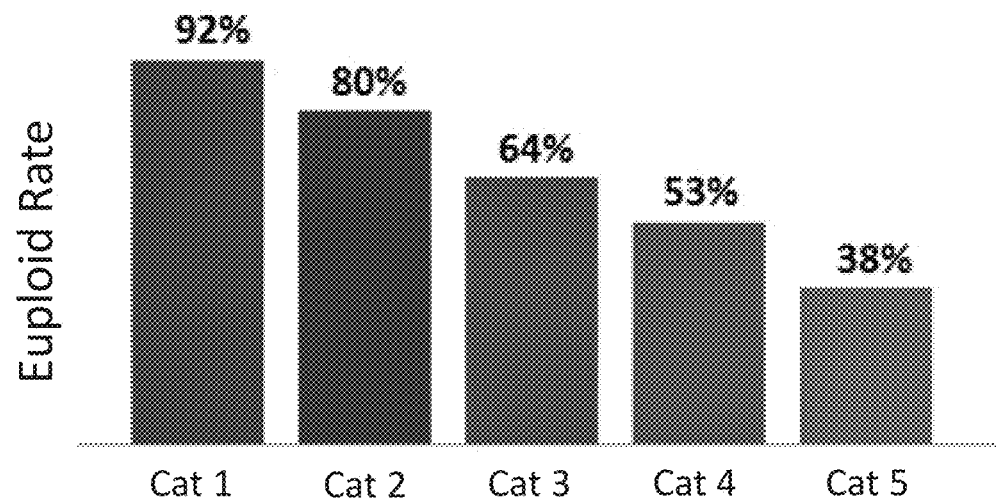
FIG. 15 is graph indicating the euploid rate of embryos placed into each of five categories.
Figure 16:
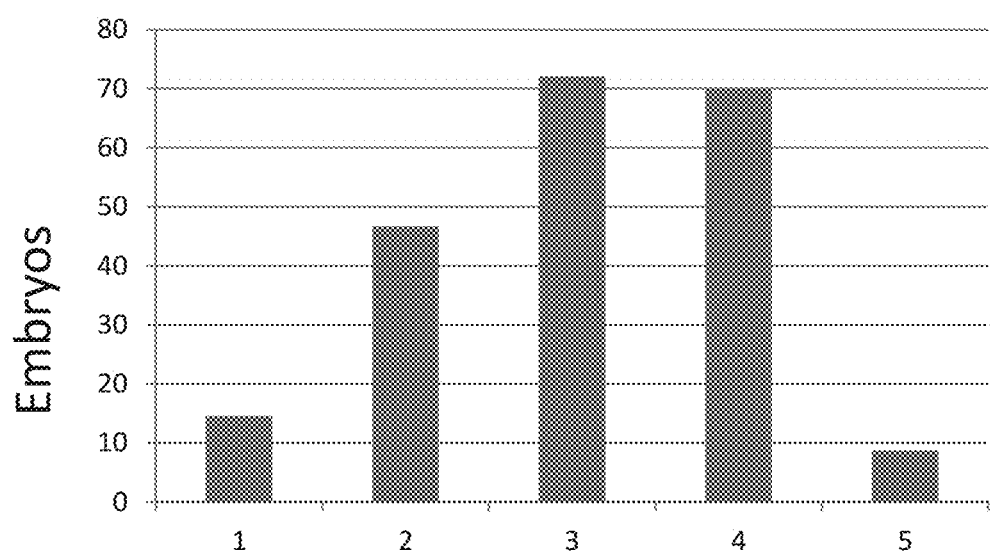
FIG. 16 is a bar graph indicating the distribution of embryos in the sample from which the bar graph of FIG. 15 was generated.

FIGS. 15 and 16 show the results of classification using age and the first 14 image features in Table 1. Specifically, FIG. 15 is a bar graph indicating the euploid rate of embryos placed into each of five categories (e.g. Cat 1, Cat 2, Cat 3, Cat 4, and Cat 5). As seen, Cat 1 has the highest euploid rate at 92%, and Cat 5 has the lowest euploid rate at 38%.

FIG. 16 is a bar graph indicating the distribution of embryos in the sample from which the bar graph of FIG. 15 was generated. As seen, Cat 1 includes approximately 14 embryos, Cat 2 includes approximately 45 embryos, Cat 3 includes approximate 72 embryos, Cat 4 includes approximately 70 embryos, and Cat 5 includes approximately 9 embryos.

Figure 17:
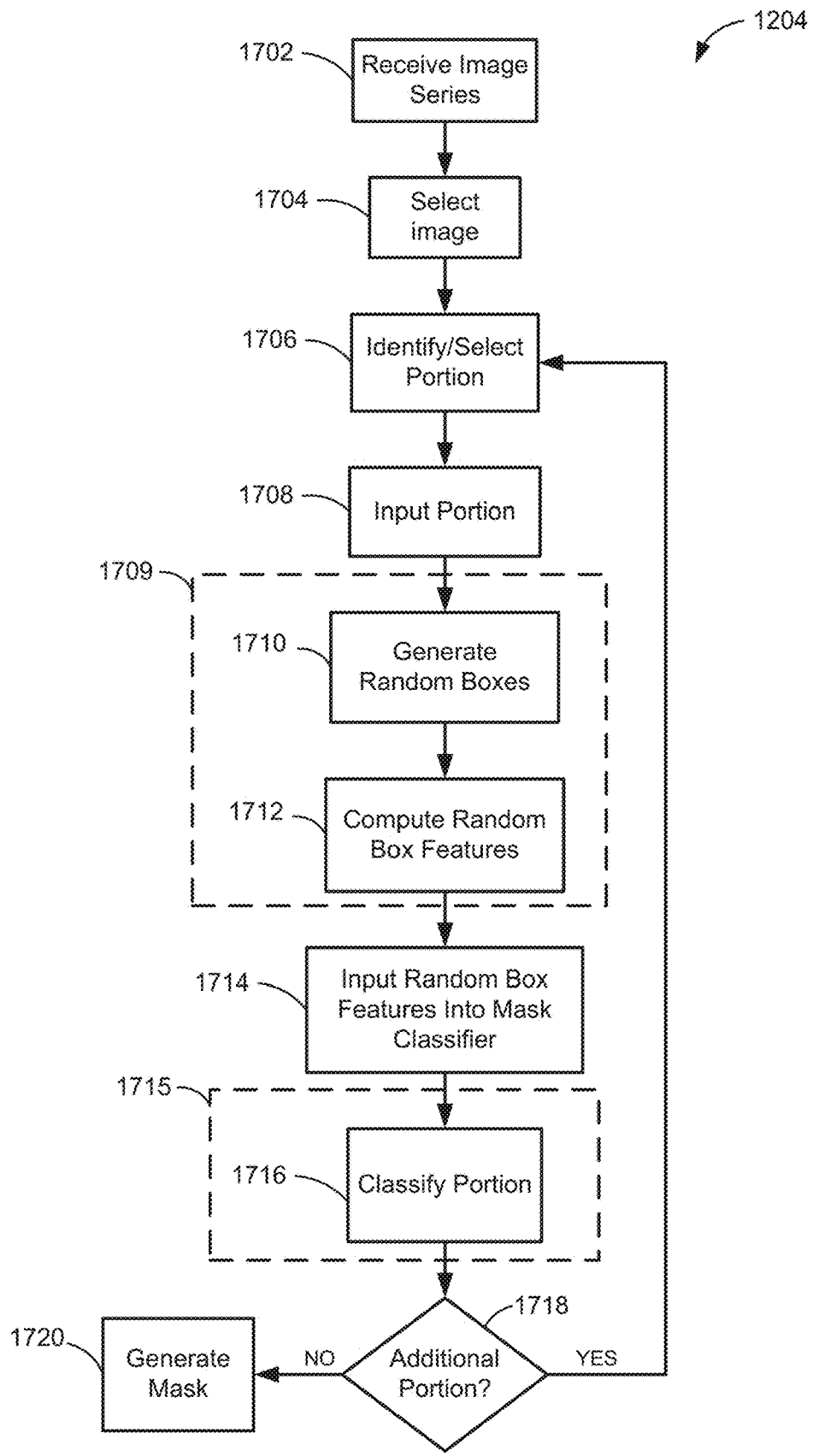
FIG. 17 is a flowchart illustrating one embodiment of a process for generation of a mask.

FIG. 17 is a flowchart illustrating one embodiment of a process 1204 for generation of a mask. In some embodiments, the process 1204 can be performed in the place of block 1204 in process 1200. The process 1204 can be performed on one or several of the images of the series of images 1201, and can be performed by the time-lapse microscope, and particularly by the server 1009 or within the microscope controller 1001.

The process 1204 begins in block 1702, wherein the series of images are received. In some embodiments, this series of images can be generated by the camera of one or several of the time lapse microscopes. After the series of images has been received, the process 1204 proceeds to block 1704, wherein one of the images from the series of images is selected for processing. In some embodiments, and in association with the selection of the one of the images from the series of images, a value indicative of selection can be associated with the selected image. This value indicative of selection can be stored in the memory 1006.

After the image has been selected, the process 1204 proceeds to block 1706, wherein a plurality of portions of the selected image are identified and one of the plurality of portions is selected. In some embodiments, these identified portions can comprise one or several equally sized and/or shaped portions of the selected. In some embodiments, each of these portions can be one or several pixels. After the portions have been identified, one of the portions can be selected for processing. In some embodiments, and in association with the selection of the one of the portions, a value indicative of selection of the portion can be associated with the selected portion. This value indicative of selection can be stored in the memory 1006.

After the portion has been identified and selected, the process 1204 proceeds to block 1706, wherein the testing portion is input into a feature module 1709. The feature module 1709 can be embodied in hardware or can be a software module. The feature module can generate one or several features for the selected portion of the selected image according to the steps of blocks 1710 and 1712.

After the inputted portion has been received by the feature module 1709, the process 1204 proceeds to block 1710 wherein one or several random boxes are generated. The random boxes can comprise areas of the selected image that can have any desired size or shape. These random boxes can be randomly located about the selected portion of the selected image.

Figure 18:
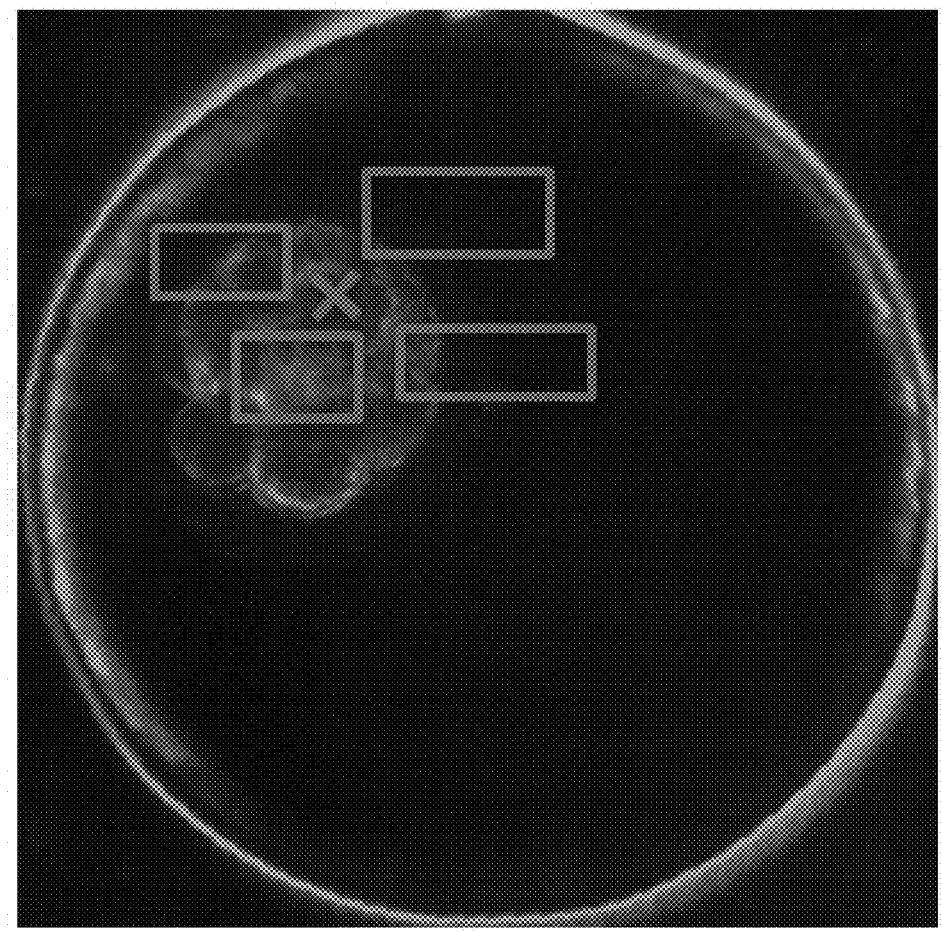
FIG. 18 is an image of an embryo within a well.

One embodiment of random boxes generated about the selected portion of the selected image as depicted in FIG. 18. In FIG. 18, an image of an embryo within a well is depicted. An "X" is located in the image, which tags identifies the location of the selected portion of the selected image, and specifically identifies the location of the selected pixel of the selected image. FIG. 18 further depicts four boxes of different sizes that are spaced about the "X." As seen, the boxes have different sizes and are spaced different distances, as measured from a box's center to the "X," from the "X."

In some embodiments, the size of the generated random boxes can be constrained within one or more size ranges. In some embodiments, these one or more size ranges can specify the maximum and/or minimum acceptable size of the generated random box. In some embodiments, a size range can include a first portion limiting a first dimension of the random box and a second portion limiting a second dimension of the random box. In one embodiment, for example, the first portion can limit the range of acceptable lengths of the random box in the second portion can limit the range of acceptable widths of the random box. In one embodiment, for example, the size range can limit the boxes to one or both of a length of between 1 and 100 pixels, between 1 and 50 pixels, between 1 and 25 pixels, between 1 and 10 pixels, between 1 and 7 pixels, between 3 and 7 pixels, between 1 and 3 pixels, and/or any other or intermediate range. In one particular embodiment, the size range can limit the boxes to a length of 3 pixels and a width between 1 and 7 pixels. In some embodiments, the random boxes can have a size ranging from [3, 1] to [3, 7], wherein the first value specifies a length of the random box and the second value specifies a width of the random box, or wherein the first value specifies a width of the random box and the second value specifies the length of the random box.

In some embodiments, the placement of the random boxes about the "X" can be restricted by a distance limit. In some embodiments, the distance limit can specify a maximum and/or minimum acceptable distance for placement of the box about the selected portion. In some embodiments, these distances are measured from the center of the selected portion to the center of the box. In some embodiments, one or both of the maximum and minimum distances can be each defined by a radius extending from the center of the selected portion. In some embodiments, the maximum distance can be, for example, defined by a first radius and the minimum distance can be defined by a second radius. In some embodiments, one or both of the first and second radii can have a length of between: 1 and 200 pixels; 1 and 150 pixels; 1 and 100 pixels; 1 and 50 pixels; 1 and 25 pixels; 1 and 10 pixels; 1 and 7 pixels; and/or any other or intermediate values. In some embodiments, the length of one or both of the first and second radii can be approximately 200 pixels, 100 pixels, 50 pixels, 25 pixels, 10 pixels, 7 pixels, 3 pixels, and/or any other or intermediate value. As used herein, "approximately" refers to a range of plus or minus 25%, 15%, 10%, 5%, or 1% of the value with which approximately is associated.

In some embodiments, any desired number of random boxes can be generated. In some embodiments, the number of generated random boxes can be selected to provide a statistically significant number of data points for determining whether the selected portion associated with the generated random boxes is inside of or outside of the mask area. In some embodiments, up to 10, 20, 30, 40, 50, 75, 100, 200, 500, 100, or any other or intermediate number of random boxes can be generated.

After the random boxes are generated, the process 1204 proceeds to block 1712, wherein random box features are calculated. The random box features can be any one or several features used to determine whether the selected portion is inside of, or outside of the mask area. In some embodiments, each of the random box features can be generated from a single random box, and in some embodiments, each of the random box features can be generated based on a pair of random boxes, which pair can be randomly generated and/or randomly paired. In some embodiments, the random box features can be based on a comparison of an image attribute of each of the random boxes in a pair of random boxes. In one embodiment, for example, the random box features can comprise the absolute value of the difference in intensity values, such as average intensity values, for pairs of random boxes.

In some embodiments the random box features can be based on information extracted from one or more random boxes and relating to the image portion contained within the one or more random boxes. In some embodiments, for example, an intensity value can be calculated for each of the random boxes. In some embodiments, this intensity value for a random box can be the average intensity of some or all of the pixels contained within that random box. In such embodiments, the intensity of the some or all of the pixels contained with the random box can be determined according to any known technique.

After the average intensity value for a random box has been determined, the image feature can be generated by determining the absolute value of the difference between the determined average intensity value and the average intensity value of the other random box of the pair of random boxes. This absolute value of the difference between the average intensity values of the pair of random boxes can be a single image feature. Further image features can be generated that are relevant to the selected portion of the image until a desired number of image features is reached. In one embodiment, for example, 50 pairs of random boxes can be used to generate 50 images features, however, in other embodiments, up to 10 image features, up to 20 image features, up to 50 image features, up to 100 image features, up to 200 image features, or any other number of image features can be generated for a selected portion of the selected image. In some embodiments, the generated image features and the therewith associated selected portions can be stored in the memory 1006.

After the random box features have been generated, the process 1204 proceeds to block 1714, wherein the random box features are inputted into a mask generation module which can be, for example, a mask classifier 1715 that can, for example, comprise one or several classifiers. Any suitable classifier may be employed in the mask classifier 1715. In some embodiments, the mask classifier 1715 is based on a machine learning algorithm. The mask classifier 1715 may be an AdaBoost (adaptive boosting) classifier, a Support Vector Machine (SVM), a Naïve Bayes classifier, a classifier using an ensemble method such as a Random Forest classifier, or a Boosting Tree.

After the random box features have been inputted into the mask classifier 1715, the process 1204 proceeds to block 1716, wherein the selected portion is classified as either being inside of the mask area or outside of the mask area. In some embodiments, this classification can be based on the application of results of a comparison of the image attributes of paired random boxes to a statistical model for example, with the mask classifier 1715. In some embodiments, this classification can be based on the training of the mask classifier 1715 and/or of a statistical model associated with and/or used by the mask classifier 1715. This training can be based on a data set, and particularly on a data set repeatedly, randomly partition into a training set and a testing set. This training can proceed as discussed above until a desired measure of effectiveness of the classifier is achieved.

As a result of the training of the classifier, the classifier can generate a viability prediction based on inputs received by the classifier. In some embodiments, a portion that is classified as belonging inside of the mask area can be associated with a first value and a portion that is classified as belonging outside of the mask area can be associated with a second value. In some embodiments, the values associated with the selected portions can be stored in the memory 1006.

After the selected portion has been classified, the process 1204 proceeds to decision block 1718, wherein it is determined if there are additional, unevaluated portions of the selected image. In some embodiments, this can include retrieving information relating to the portion of the selected image from the memory 1006, and determining if a value indicative of selection and evaluation has been associated with all of the portions of the selected image.

If it is determined that there are additional unevaluated portions of the selected image, then the process 1204 returns to block 1704, and proceeds as outlined above. In some embodiments, this can result in the iterative selection and evaluation of the portions of the selected image until some or all of the portions of the selected image have been evaluated and/or classified as belonging inside of the mask area or outside of the mask area. This iterative selection and evaluation of the portions of the selected image can include the generation of random boxes for each of the iteratively selected portions, and the identification of each of the iteratively selected points as either belonging inside of the mask area or outside of the mask area.

Returning again to decision block 1718, if it is determined that there are no unevaluated portions of the selected image, then the process 1204 proceeds to block 1720 and a mask is generated for the selected image, and specifically, a preliminary mask is generated for the selected image. In some embodiments, the generation of the preliminary mask can include identifying and grouping all of the portions of the selected image designated as outside of the mask area and/or all of the portions of the selected image designated as inside of the mask area.

In some embodiments, and after the mask is generated for the selected image, the process 1204 can further determine if there are additional, unselected images in the series of images. In some embodiments, this can include determining if a value indicative of selection and evaluation has been associated with all of the images in the series of images. If it is determined that all of the images in the series of images have not been selected, then the process 1204 can return to block 1704 and proceed as outlined above. If it is determined that all of the images in the series of images have been selected, then the process 1200 can proceed to block 1206.

Figure 19:
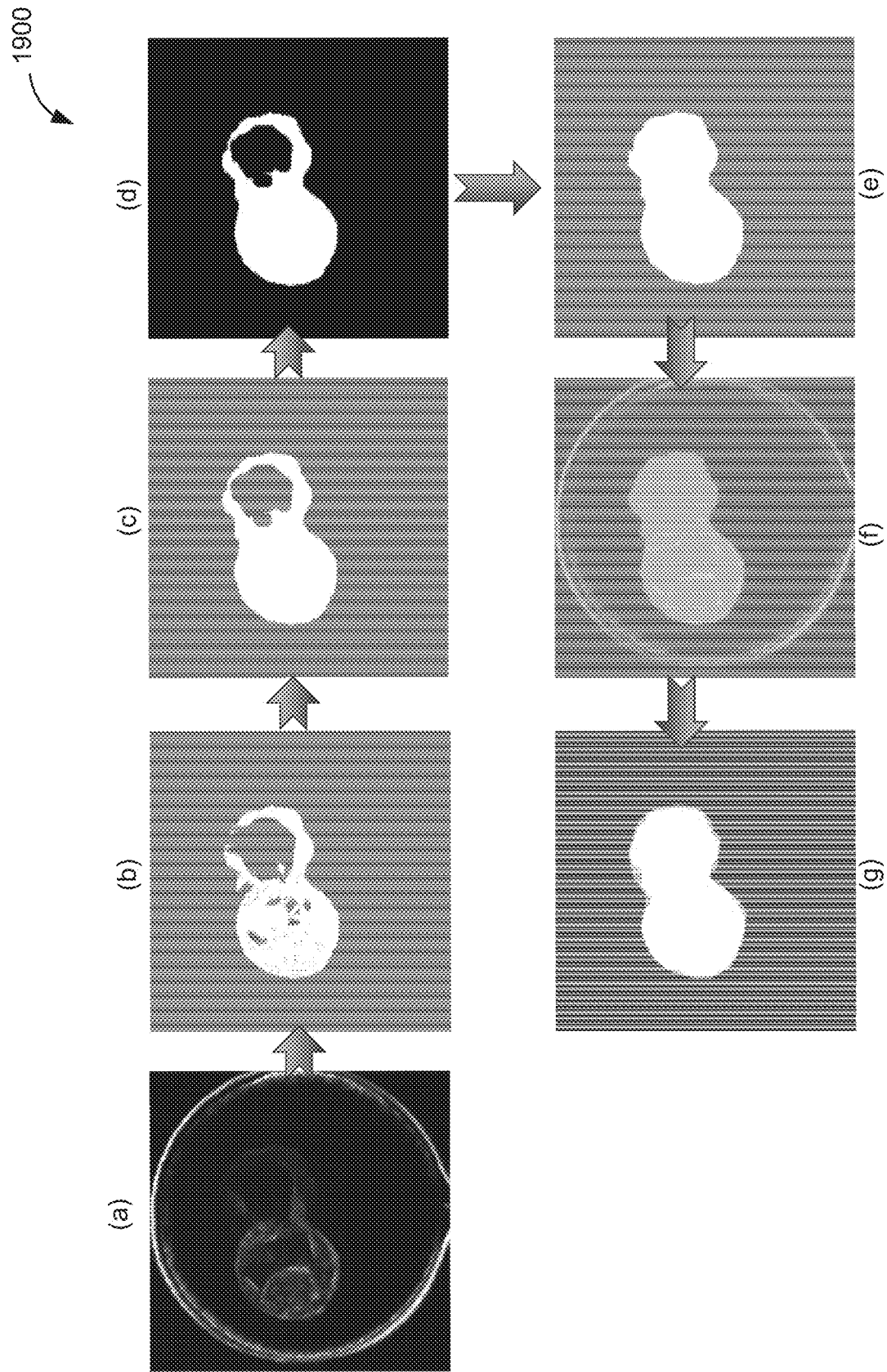
FIG. 19 is a schematic illustration of one embodiment of a process for generation of a final mask.

FIG. 19 is a schematic illustration of one embodiment of a process 1900 for generation of a final mask and/or first and second masks from a preliminary mask. This process 1900 is depicted by a series of images of a mask created for a hatching embryo, and of the comparison of that mask to the embryo image. These images progress, starting with image (a) and ending with image (g). In these images, the zona pellucida and the area enclosed by the zona pellucida forms the left-most, white, spherical portion, and the blastocycst as defined by the trophectoderm forms the right-most, white portions of the image. In images (b), (c), and (d), the cavity within the blastocyst is visible as the black enclosed area within the right-most, white portion of the image. This cavity portion is filled, and thus appears white in images (e) and (g).

The images (a)-(g) start with image (a) which depicts the image of an embryo within the well having visible well walls forming a circle around the embryo. The preliminary mask is depicted in image (b). This preliminary mask is the output of process 1204. As seen in image (b), the preliminary mask can include one or several holes (see as black portions within the left-most, white, circular portion of the image (b).

As further seen in image (b), the indicia of the well captured in image (a) have been removed and/or obscured by the mask. In some embodiments, indicia of the well such as the well wall can be identified and removed via, for example, the use of the random box technique discussed above, and/or via any other desired post-processing technique.

After the preliminary mask is been generated, the process 1900 proceeds to refine the preliminary mask. In some embodiments, the refinement can include identifying one or several continuous, foreground components. These components can be identified via Connected Component Analysis, and in some embodiments, all but one or several designated identified components can be removed from the foreground, and particularly, all but the largest one or several of these components can be removed from the foreground. In some embodiments, Connected Component Analysis can be performed using any commercially or open source available Connected Component Analysis software or code.

The refinement can further include the identification and filing of one or several holes enclosed, or partially enclosed within the foreground portions of the mask. This can be performed via hole filing, dilation, or other post processing technique. In some embodiments, the hole filing and/or dilation can be performed using available hole filing and/or dilation software or code.

In some embodiments, the hole filing can include, for example: adding a boundary to the preliminary mask between the foreground and background portions; inverting the image so that what was background is now foreground; region growing the connected component that was background but is now foreground to generate a continuous body of the foreground that was the background. The region can be grown starting from a seed that can be, for example, in any corner of the image.

After the continuous body has been generated, the image can be inverted, and holes in the continuous body can be identified. In some embodiments, these holes can be identified, for example, by evaluation of the continuous body for discontinuities and/or changes in pixel intensity within the continuous body. In some embodiments, for example, the continuous body can have a single color and/or intensity, and thus any change or discontinuity in intensity or color within the continuous body can indicate a hole.

After the hole has been identified, the identified holes can be removed from the foreground, and thereby filled. In some embodiments, these holes can be filled based on one or several connectivity parameters. In one embodiment, for example, the one or several connectivity parameters can allow for filing of pixels in holes that are, for example, 4-connected, 8-connected, or the like. After the holes have been removed and thereby filled, the boundary can be removed. In some embodiments, the hole filing can be iterated to improve the quality of the mask.

Through the Connected Component Analysis and the hole filing, the mask can be refined such that the foreground and background portions of the mask are more continuous as depicted in images (c), (d), and (e). In some embodiments, this refinement can be an iterative process involving repeated steps. In the images of FIG. 19, image (c) has been iteratively less-refined than either image (d) or image (e). Thus, as seen in images (c) and (d), the cavity is still unfilled in the right-most, white portion of the image. Accordingly, the cavity of the embryo is in the background. As further seen in images (c) and (d), the white image portions surrounding the cavity are more continuous than in image (b) and the holes have been removed from left-most, white portion of the images (c) and (d).

In some embodiments, the first mask, as discussed above with respect to FIG. 13, consistent with one of images (c) and (d) can be created. Further, in some embodiments, the second mask, as discussed above with respect to FIG. 13, consistent with image (e) can be created. In some embodiments, the first and second masks can have the same outer boundary and can differ only in that the area of the cavity is obscured in the first mask and unobscured in the second mask. These masks can be stored in, for example, the memory 1006.

In some embodiments in which the quality of the generated masks is being evaluated, one or both of the generated first and second masks can be applied, superimposed, and/or overlaid on the image of the embryo to identify the degree of overlap of the masks with the image of the embryo. The applying, superimposing, and/or overlaying of the masks on the image of the embryo is shown in images (f) and (g). In some embodiments, the degree of overlap between the image of the embryo and one or both of the first and second masks can be used to determine the accuracy of the one or both of the first and second masks. In some embodiments, a Dice coefficient can be used to calculate the degree of overlap between the masks and the image of the embryo.

Figure 20:
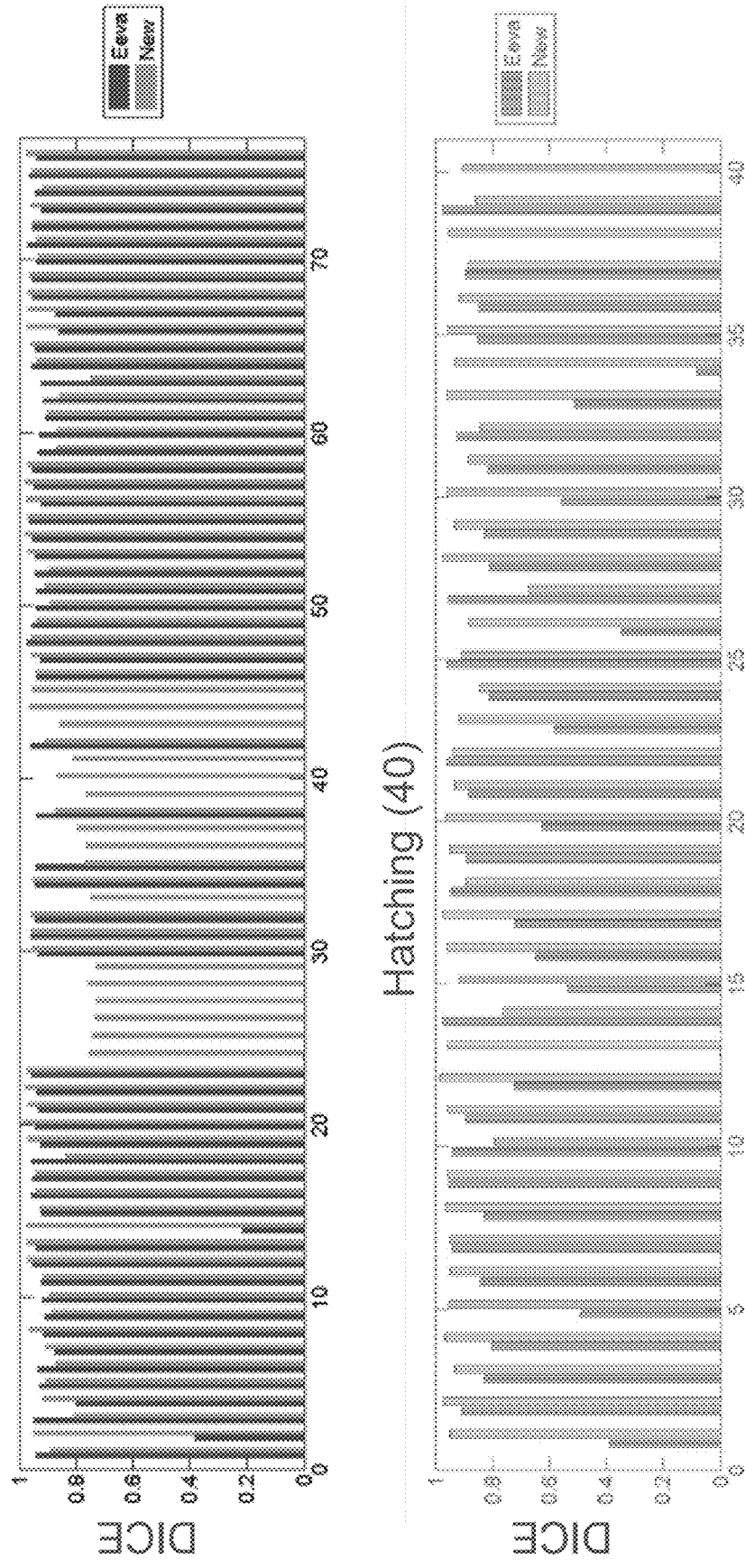
FIG. 20 is a bar chart showing the comparison of Dice coefficients for an old mask and a new mask.
Figure 21:
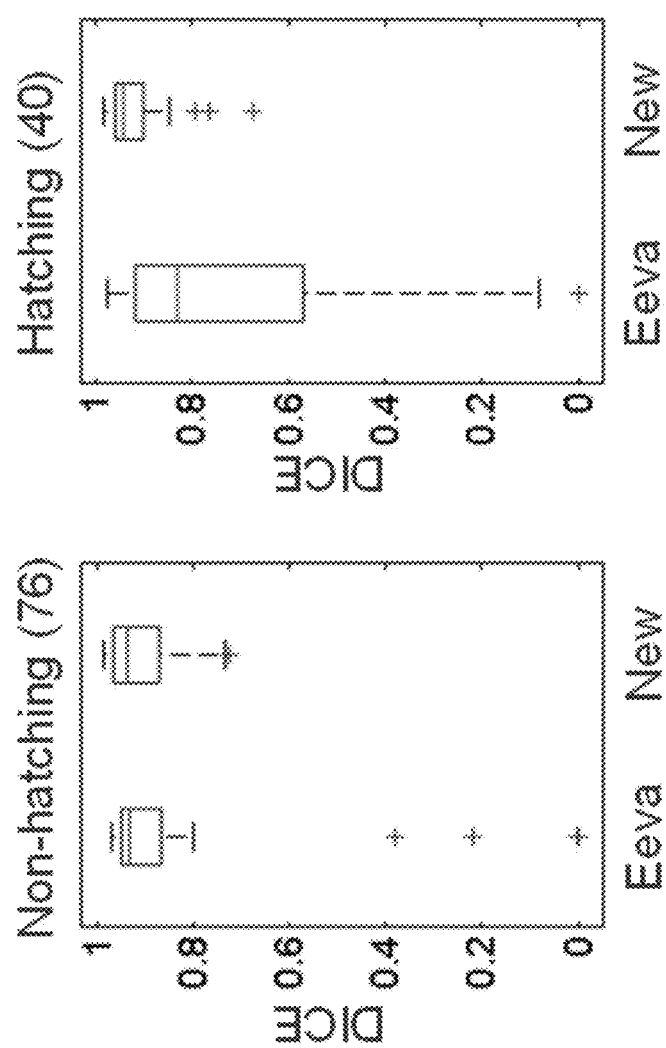
FIG. 21 is a boxchart showing the comparison of Dice coefficients for an old mask and a new mask.

FIGS. 20 and 21 are charts showing Dice coefficients for an old mask (labeled Eeva) and the new mask as disclosed herein (labeled new). In FIG. 20, the top graph indicates the Dice coefficients for both old and new masks for 76 non-hatching samples, and the bottom graph indicates the Dice coefficients for both the old and new masks for 40 hatching samples. As seen in both graphs, the new mask performs more consistently than the old mask across all samples.

In FIG. 21, boxplots of the data from FIG. 20 are shown. As seen in these boxplots, the old and new masks perform similarly for non-hatching samples, but the new mask performs significantly better than the old mask for hatching samples as the new mask provides more consistent results. Accordingly, the new mask is better suited for application after day-3 of embryo development.

Figure 22:
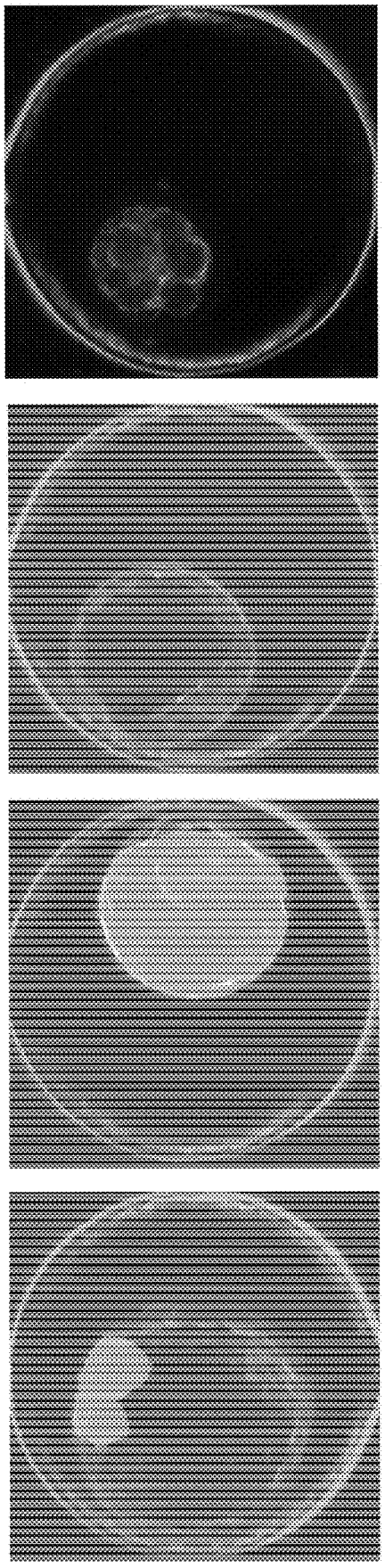
FIG. 22 includes sets of images of non-hatching embryos overlaid by the old and new masks.
Figure 22:
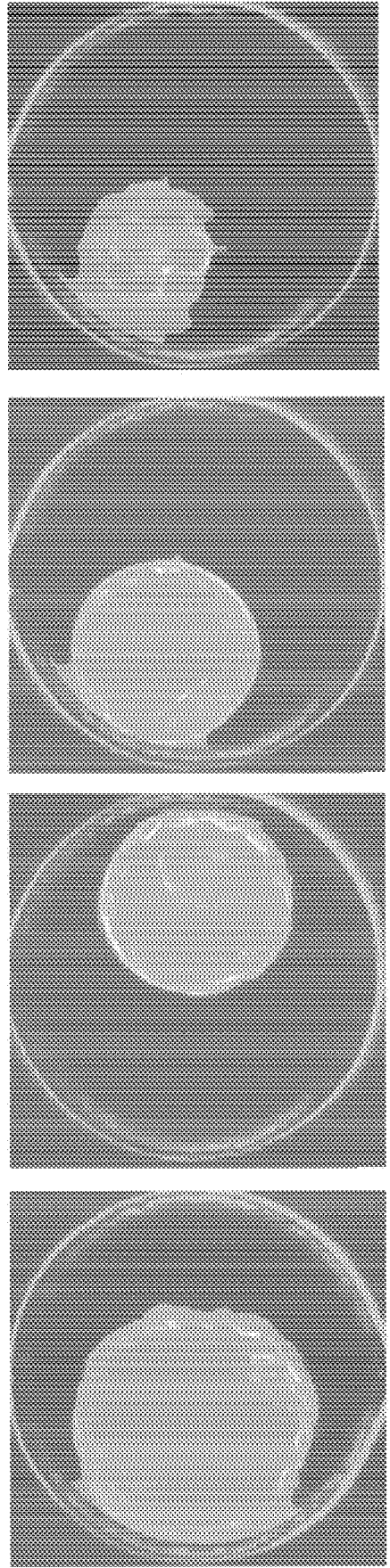
Figure 23:
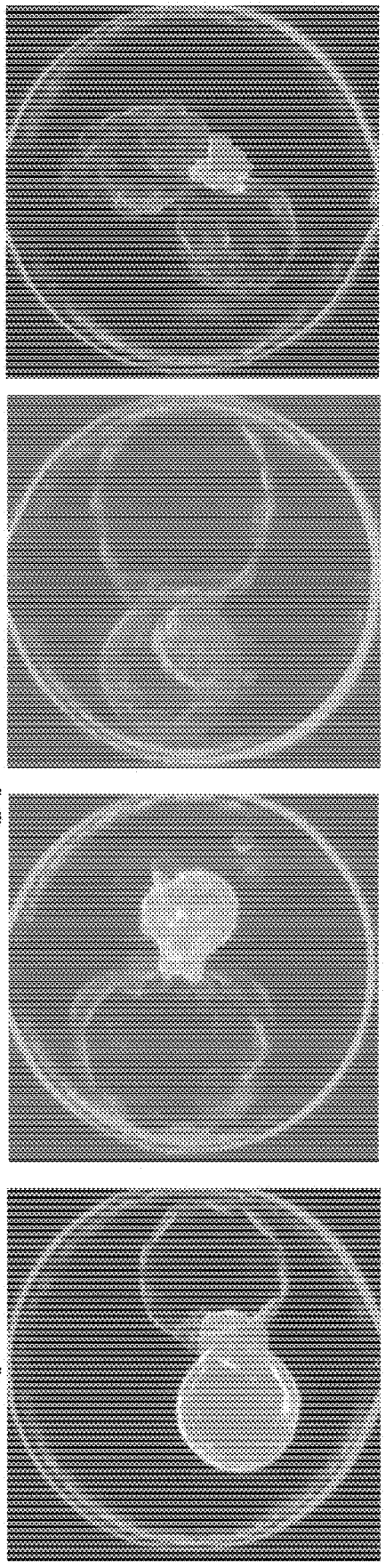
FIG. 23 includes sets of images of hatching embryos overlaid by the old and new masks.
Figure 23:
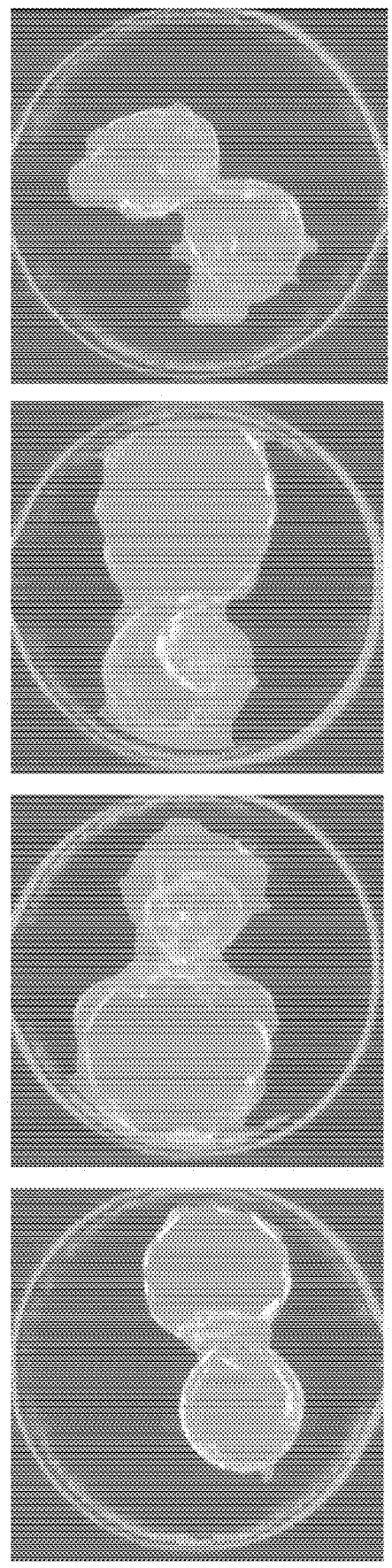

FIGS. 22 and 23 are images showing comparison of the performance of the old mask versus the new mask with respect to collected images of embryos. FIG. 22 includes two sets of the same four images. Specifically, FIG. 22 includes a first set of four top images that show the overlaying of the old mask on embryo images, in which hatching is not occurring, a second set of four, bottom images that show the overlaying of the new mask on the same embryo images. The embryo images in FIG. 22 are non-hatching. As seen in these images, the new masks more consistently overlays the embryo images than the old masks.

FIG. 23 includes two sets of the same four images. Specifically, FIG. 23 includes a first set of four top images that show the overlaying of the old mask on embryo images, in which hatching is occurring, a second set of four, bottom images that show the overlaying of the new mask on the same embryo images. The embryo images in FIG. 23 are assisted-hatching. As seen in these images, the new masks more consistently overlays the embryo images than the old masks.

An embodiment of the invention relates to a computer storage product with a computer-readable medium having computer code thereon for performing various computer-implemented operations. The term "computer-readable medium" is used herein to include any medium that is capable of storing or encoding a sequence of instructions or computer codes for performing the operations described herein. The media and computer code may be those specially designed and constructed for the purposes of the invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the invention may be implemented using Java, C++, or other object-oriented programming language and development tools. Additional examples of computer code include encrypted code and compressed code. Moreover, an embodiment of the invention may be downloaded as a computer program product, which may be transferred from a remote computer (e.g., a server computer) to a requesting computer (e.g., a client computer or a different server computer) via a transmission channel. Another embodiment of the invention may be implemented in hardwired circuitry in place of, or in combination with, machine-executable software instructions.

An embodiment of the invention can be implemented in hardware, such as a field programmable gate array (FPGA) or ASIC. The FPGA/ASIC may be configured by and may provide output to input/output devices.

The preceding merely illustrates the principles of the invention. It is appreciated that those skilled in the art may be able to devise various arrangements which, although not explicitly described or shown herein, embody the principles of the invention and are included within its spirit and scope. The illustrations may not necessarily be drawn to scale, and manufacturing tolerances may result in departure from the artistic renditions herein. There may be other embodiments of the present invention which are not specifically illustrated. Thus, the specification and the drawings are to be regarded as illustrative rather than restrictive. Additionally, the drawings illustrating the embodiments of the present invention may focus on certain major characteristic features for clarity. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims. In addition, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention. All references cited herein are incorporated by reference in their entireties.

What is claimed is:

1. A method for determining viability of a human embryo, the method comprising:
   receiving an image comprising a human embryo from an imaging system, said image comprising a plurality of pixels, wherein at least one pixel is selected from said plurality of pixels;
   generating a plurality of random boxes on said image, said plurality of random boxes are located around said at least one selected pixel, and wherein said plurality of random boxes have a plurality of random sizes and a plurality of random locations;
   identifying that said at least one selected pixel within at least one of said plurality of random boxes is inside said at least one human embryo or outside said at least one human embryo such that an embryo mask is superimposed on the received image wherein the embryo mask distinguishes between a first portion of the image and a second portion of the image, wherein the first portion contains the image of the embryo, and wherein the second portion does not contain the image of the embryo;
   pairing said plurality of random boxes to detect a feature of the image based on the first portion of the image; and
   generating a viability prediction based on the detected feature of the image such that the viability prediction recommends selection of the human embryo based upon a predicted likelihood of implantation; and
   implanting the selected human embryo in a human.

2. The method of claim 1, wherein the image based feature is selected from the group consisting of embryo image area; cavity image area; a change in embryo image area over time; a change in cavity image area over time; embryo image perimeter; and convex hull.

3. The method of claim 1, wherein the image based feature is selected from the group consisting of cavitation; hatching; embryo expansion; and embryo collapse.

4. The method of claim 1, wherein the image-based features is selected from the group consisting of an area of the embryo; an area of a cavity of the embryo; a perimeter of the embryo; and a convex hull.

5. The method of claim 1, wherein the viability prediction further comprises a prediction of euploidy in the human embryo.

6. An imaging system for evaluation of a human embryo, the system comprising:
   a stage configured to receive a multi-well culture dish comprising a plurality of micro-wells, wherein each of said plurality of micro-wells contain at least one human embryo;
   a time-lapse microscope configured to:
      acquire a series of time-lapse images of the at least one human embryo;
      select an image of the at least one human embryo from the series of time-lapse images, said image comprising a plurality of pixels;
      generate a plurality of random boxes having a random location and a random size that are located around said plurality of pixels to superimpose an embryo mask on the received image, wherein the embryo mask distinguishes between a first portion of the image and a second portion of the image;

detect a feature of the image based on at least one pairing of said plurality of random boxes; and generate a viability prediction that determines a developmental potential for implantation of the at least one human embryo based on the detected image based feature; and a mask classifier software module configured to pair said plurality of random boxes around at least one pixel of said plurality of pixels to detect at least one feature of said at least one embryo.

7. The imaging system of claim 6, wherein the image based feature is selected from the group consisting of embryo image area; cavity image area; a change in embryo image area over time; a change in cavity image area over time; embryo image perimeter; and convex hull.

8. The imaging system of claim 6, wherein the image based feature is selected from the group consisting of cavitation; hatching; embryo expansion; and embryo collapse.

9. The imaging system of claim 6, wherein the image based feature is selected from the group consisting of an area of the embryo; an area of a cavity of the embryo; a perimeter of the embryo; and a convex hull.

* * * * *